(12) United States Patent
van Walsem et al.

(10) Patent No.: US 10,786,064 B2
(45) Date of Patent: Sep. 29, 2020

(54) PROCESS FOR PRODUCING A MONOMER COMPONENT FROM A GENETICALLY MODIFIED POLYHYDROXYALKANOATE BIOMASS

(75) Inventors: Johan van Walsem, Acton, MA (US); Erik Anderson, Somerville, MA (US); John Licata, Wakefield, MA (US); Kevin A. Sparks, Scituate, MA (US); Christopher Mirley, Winthrop, MA (US); M. S. Sivasubramanian, Wayland, MA (US)

(73) Assignee: CJ CHEILJEDANG CORPORATION, Seoul (KR)

( * ) Notice: Subject to any disclaimer, the term of this patent is extended or adjusted under 35 U.S.C. 154(b) by 648 days.

(21) Appl. No.: 13/578,044

(22) PCT Filed: Feb. 11, 2011

(86) PCT No.: PCT/US2011/024620
§ 371 (c)(1),
(2), (4) Date: Aug. 9, 2012

(87) PCT Pub. No.: WO2011/100608
PCT Pub. Date: Aug. 18, 2011

(65) Prior Publication Data
US 2012/0315681 A1    Dec. 13, 2012

Related U.S. Application Data

(60) Provisional application No. 61/303,584, filed on Feb. 11, 2010, provisional application No. 61/382,855, filed on Sep. 14, 2010, provisional application No. 61/413,195, filed on Nov. 12, 2010.

(51) Int. Cl.
| | | |
|---|---|---|
| *C12P 7/62* | (2006.01) |
| *C12P 7/42* | (2006.01) |
| *C07C 57/08* | (2006.01) |
| *A45D 40/00* | (2006.01) |
| *C07D 319/12* | (2006.01) |
| *C07D 407/04* | (2006.01) |
| *C07D 305/12* | (2006.01) |
| *C07D 307/33* | (2006.01) |
| *C07D 309/30* | (2006.01) |
| *C12P 7/52* | (2006.01) |
| *C12P 17/04* | (2006.01) |
| *C07C 67/08* | (2006.01) |
| *C07C 67/333* | (2006.01) |

(52) U.S. Cl.
CPC .......... *A45D 40/0068* (2013.01); *C07C 67/08* (2013.01); *C07C 67/333* (2013.01); *C07D 305/12* (2013.01); *C07D 307/33* (2013.01); *C07D 309/30* (2013.01); *C07D 319/12* (2013.01); *C07D 407/04* (2013.01); *C12P 7/52* (2013.01); *C12P 7/625* (2013.01); *C12P 17/04* (2013.01)

(58) Field of Classification Search
CPC .......... C08L 67/04; C07C 57/08; C12P 7/625; C12N 15/52
USPC ........................ 435/135, 257.1; 524/317, 599
See application file for complete search history.

(56) References Cited

U.S. PATENT DOCUMENTS

| | | |
|---|---|---|
| 2,361,036 A | 10/1944 | Kung |
| 3,720,689 A | 3/1973 | Pohl et al. |
| 3,859,386 A | 1/1975 | Mainord |
| 4,031,115 A | 6/1977 | Kurkov |
| 4,101,533 A | 7/1978 | Lafferty et al. |
| 4,129,711 A | 12/1978 | Viout et al. |
| 4,193,896 A | 3/1980 | Cook |
| 4,230,643 A | 10/1980 | Eichhorn et al. |
| 4,234,907 A | 11/1980 | Daniel |
| 4,309,357 A | 1/1982 | Chiusoli et al. |
| 4,324,880 A | 4/1982 | Dhein et al. |
| 4,365,088 A | 12/1982 | Vanlautem et al. |
| 4,435,534 A | 3/1984 | Jones et al. |
| 4,465,634 A | 8/1984 | Chiusoli et al. |
| 4,489,188 A | 12/1984 | Jones et al. |
| 4,525,512 A | 6/1985 | Hudson |
| 4,649,170 A | 3/1987 | Reid |
| 4,652,685 A | 3/1987 | Cawse et al. |
| 4,851,085 A | 7/1989 | De Thomas |
| 4,876,331 A | 10/1989 | Doi |
| 4,876,368 A | 10/1989 | Broussard et al. |
| 4,910,145 A | 3/1990 | Holmes et al. |
| 4,935,052 A | 6/1990 | Huppatz et al. |
| 4,968,611 A | 11/1990 | Traussnig et al. |
| 4,997,976 A | 3/1991 | Brunengraber et al. |

(Continued)

FOREIGN PATENT DOCUMENTS

| | | |
|---|---|---|
| CA | 2 625 511 A1 | 3/2008 |
| EP | 0 069 497 A2 | 1/1983 |

(Continued)

OTHER PUBLICATIONS

Ariffin et al. Pol. Deg stab 2008, 93, pp. 1433-1439.*

(Continued)

*Primary Examiner* — Robert B Mondesi
*Assistant Examiner* — Mohammad Y Meah
(74) *Attorney, Agent, or Firm* — Christensen, Fonder, Dardi; Diane E. Bennett; Peter S. Dardi

(57) ABSTRACT

The patent application relates to a method of producing a monomer component from a genetically modified polyhydroxyalkanoate (PHA) biomass, wherein the biomass is heated in the presence of a catalyst to release a monomer component from the PHA.

21 Claims, 12 Drawing Sheets

(56) References Cited

U.S. PATENT DOCUMENTS

| | | |
|---|---|---|
| 5,066,657 A | 11/1991 | Hayashi et al. |
| 5,107,016 A | 4/1992 | Pennetreau |
| 5,112,865 A | 5/1992 | Nichels et al. |
| 5,141,924 A | 8/1992 | Bolin |
| 5,145,989 A | 9/1992 | Dougherty et al. |
| 5,186,744 A | 2/1993 | Bodwell et al. |
| 5,213,976 A | 5/1993 | Blauhut et al. |
| 5,229,528 A | 7/1993 | Brake et al. |
| 5,236,987 A | 8/1993 | Arendt |
| 5,245,023 A | 9/1993 | Peoples et al. |
| 5,250,430 A | 10/1993 | Peoples et al. |
| 5,264,614 A | 11/1993 | Brake |
| 5,270,147 A | 12/1993 | Van Thillo et al. |
| 5,286,842 A | 2/1994 | Kimura |
| 5,292,860 A | 3/1994 | Shiotani et al. |
| 5,352,763 A | 10/1994 | Yamaguchi et al. |
| 5,455,221 A | 10/1995 | Cutler et al. |
| 5,461,139 A | 10/1995 | Gonda et al. |
| 5,480,794 A | 1/1996 | Peoples et al. |
| 5,512,669 A | 4/1996 | Peoples et al. |
| 5,516,883 A | 5/1996 | Hori et al. |
| 5,534,432 A | 7/1996 | Peoples et al. |
| 5,563,239 A | 10/1996 | Hubbs et al. |
| 5,665,831 A | 9/1997 | Neuenschwander et al. |
| 5,750,751 A | 5/1998 | Saam |
| 5,894,062 A | 4/1999 | Liddell |
| 5,897,669 A | 4/1999 | Matsui |
| 5,928,781 A | 7/1999 | Caines et al. |
| 5,942,597 A | 8/1999 | Noda et al. |
| 6,008,184 A | 12/1999 | Pluyter et al. |
| 6,043,063 A | 3/2000 | Kurdikar et al. |
| 6,087,471 A | 7/2000 | Kurdikar et al. |
| 6,110,998 A | 8/2000 | Slinkard et al. |
| 6,117,658 A | 9/2000 | Dennis et al. |
| 6,323,010 B1 | 11/2001 | Skraly et al. |
| 6,329,183 B1 | 12/2001 | Skraly et al. |
| 6,623,730 B1 | 9/2003 | Williams et al. |
| 6,831,182 B2 | 12/2004 | Borchert et al. |
| 6,852,517 B1 | 2/2005 | Suthers et al. |
| 6,897,338 B2 | 5/2005 | Zhong et al. |
| 7,166,743 B2 | 1/2007 | Zhong et al. |
| 7,229,804 B2 | 6/2007 | Huisman et al. |
| 7,252,980 B2 | 8/2007 | Walsem et al. |
| 7,641,706 B1 | 1/2010 | McMurry et al. |
| 7,687,661 B2 | 3/2010 | Lilga et al. |
| 8,026,386 B2 | 9/2011 | Burk et al. |
| 8,048,624 B1 | 11/2011 | Lynch |
| 8,084,626 B1 | 12/2011 | Fruchey et al. |
| 8,100,990 B2 | 1/2012 | Ellens et al. |
| 8,113,643 B2 | 2/2012 | Sarkisian et al. |
| 8,114,643 B2 | 2/2012 | Skraly et al. |
| 8,124,388 B2 | 2/2012 | Liao et al. |
| 8,129,154 B2 | 3/2012 | Burk et al. |
| 9,084,467 B2 | 7/2015 | van Walsem et al. |
| 9,850,192 B2 | 12/2017 | Harris et al. |
| 2004/0253693 A1 | 12/2004 | Hein et al. |
| 2007/0107080 A1 | 5/2007 | Liao et al. |
| 2008/0199926 A1 | 8/2008 | Burgard et al. |
| 2009/0064567 A1 | 3/2009 | Lippmeier et al. |
| 2009/0075351 A1 | 3/2009 | Burk et al. |
| 2009/0155866 A1 | 6/2009 | Burk et al. |
| 2009/0264672 A1 | 10/2009 | Abraham et al. |
| 2009/0318647 A1* | 12/2009 | Hagadorn ............ C08F 210/06 526/171 |
| 2009/0325248 A1 | 12/2009 | Marx et al. |
| 2010/0145086 A1 | 6/2010 | Schrodi et al. |
| 2010/0228067 A1 | 9/2010 | Peterson et al. |
| 2010/0291644 A1 | 11/2010 | Marx et al. |
| 2010/0304453 A1 | 12/2010 | Trawick et al. |
| 2011/0045575 A1 | 2/2011 | van Dien et al. |
| 2011/0144377 A1 | 6/2011 | Eliot et al. |
| 2011/0217742 A1 | 9/2011 | Sun et al. |
| 2011/0319849 A1 | 12/2011 | Collias et al. |
| 2012/0078004 A1 | 3/2012 | Fruchey et al. |
| 2012/0122952 A1 | 5/2012 | Tung |
| 2012/0129232 A1 | 5/2012 | Skraly et al. |
| 2012/0225461 A1 | 9/2012 | Dole et al. |
| 2012/0315681 A1 | 12/2012 | van Walsem et al. |
| 2013/0046075 A1 | 2/2013 | Van Walsem et al. |
| 2013/0122541 A1 | 5/2013 | Lynch et al. |
| 2013/0288317 A1 | 10/2013 | Ramseier et al. |
| 2014/0024769 A1 | 1/2014 | van Walsem et al. |
| 2014/0114082 A1 | 4/2014 | van Walsem et al. |
| 2014/0170714 A1 | 6/2014 | van Walsem et al. |
| 2014/0234944 A1 | 8/2014 | Zhang et al. |
| 2015/0159184 A1 | 6/2015 | Ramseier et al. |
| 2015/0376152 A1 | 12/2015 | Samuelson et al. |
| 2017/0009008 A1 | 1/2017 | Van Walsem et al. |

FOREIGN PATENT DOCUMENTS

| | | |
|---|---|---|
| EP | 0 392 687 A2 | 10/1990 |
| EP | 2 025 760 A1 | 2/2009 |
| EP | 2 360 137 A1 | 8/2011 |
| GB | 1120427 A | 7/1968 |
| JP | 3178949 | 8/1991 |
| JP | 3231904 B2 | 11/2001 |
| JP | 2002-225952 | 9/2011 |
| JP | 6087784 B2 | 3/2017 |
| WO | WO-94/11440 A2 | 5/1994 |
| WO | WO-94/11440 A3 | 5/1994 |
| WO | WO 1996/035796 A1 | 11/1996 |
| WO | WO-98/36078 A1 | 8/1998 |
| WO | WO-98/39453 A1 | 9/1998 |
| WO | WO-98/46782 A1 | 10/1998 |
| WO | WO 1999/14313 A2 | 3/1999 |
| WO | WO 1999/14313 A3 | 3/1999 |
| WO | WO-99/61624 A2 | 12/1999 |
| WO | WO-99/61624 A3 | 12/1999 |
| WO | WO-99/64078 A2 | 12/1999 |
| WO | WO-99/64078 A3 | 12/1999 |
| WO | WO-00/08198 A1 | 2/2000 |
| WO | WO 2002/042418 A2 | 5/2002 |
| WO | WO 03/051813 A1 | 6/2003 |
| WO | WO 2005/095320 A1 | 10/2005 |
| WO | WO 2009/046929 A2 | 4/2009 |
| WO | WO 2010/006076 A2 | 1/2010 |
| WO | WO 2010/006076 A3 | 1/2010 |
| WO | WO 2010/007327 A2 | 1/2010 |
| WO | WO 2010/007327 A3 | 1/2010 |
| WO | WO 2010/030711 A2 | 3/2010 |
| WO | WO 2010/044112 A1 | 4/2010 |
| WO | WO 2010/068953 A3 | 6/2010 |
| WO | WO 2010/092155 A1 | 8/2010 |
| WO | WO 2010/092304 A2 | 8/2010 |
| WO | WO 2010/141920 A2 | 12/2010 |
| WO | WO 2011/038364 A1 | 3/2011 |
| WO | WO 2011/100601 A1 | 8/2011 |
| WO | WO-2011/100608 A1 | 8/2011 |
| WO | WO 2011/154503 A1 | 12/2011 |
| WO | WO-2012/001003 A1 | 1/2012 |
| WO | WO 2012/149162 A2 | 11/2012 |
| WO | WO 2012/170793 A1 | 12/2012 |
| WO | WO 2012/170793 A8 | 12/2012 |
| WO | WO 2013/023140 A1 | 2/2013 |
| WO | WO 2013/023140 A8 | 2/2013 |
| WO | WO 2013/082264 A1 | 6/2013 |
| WO | WO 2013/085361 A2 | 6/2013 |
| WO | WO 2013/142033 A1 | 9/2013 |
| WO | WO 2013/185009 A1 | 12/2013 |
| WO | WO 2014/127053 A2 | 8/2014 |
| WO | WO 2014/210535 A2 | 12/2014 |
| WO | WO 2014/210535 A3 | 12/2014 |

OTHER PUBLICATIONS

Yunus et al. Asia Pac J. Mol Biol and Biotech 2008 16 pp. 1-10.*
Gartside et al. PTQ Q2, 2006 pp. 1-7.*
Sudborough etal. RSC, 1909, pp. 315-313.*
Weerasinghe et al. ADv chem pross, 2000, pp. 1037-1042.*
Mukaiyama et al. chem let., 1992, pp. 625-628.*
Notification of Transmittal of the International Search Report and the Written Opinion of the International Searching Authority, or the

(56) References Cited

OTHER PUBLICATIONS

Declaration, for International Application No. PCT/US2011/024620, dated Jul. 6, 2011, consisting of 15 pages.
Abe, H., "Thermal Degradation of Environmentally Degradable Poly(Hydroxyalkanoic Acid)s," Macromolecular Bioscience, 6:469-486 (2006).
Morikawa, H., et al., "Pyrolysis of Bacterial Polyalkanoates," Canadian Journal of Chemistry, 59:2306-2313 (1981).
International Preliminary Report on Patentability, PCT/US/2011/024620, dated Aug. 23, 2012.
Kim, et al., "Effects of Residual Metal Compounds and Chain End Structure on Thermal Degradation of P3HB", *Polymer Degradation and Stability*, 91, p. 769, 2006.
Kim, et al., "Effect of Metal Compounds on the Thermal Degradation Behavior of Aliphatic Poly(hydroxyalkanoic Acids", *Polymer Degradation and Stability*, 93, p. 776, 2008.
Kopinke, et al., "Thermal Decomposition of Biodegradable Polyesters—1:Polyhdyroxybutyric Acid", *Polymer Degradation and Stability*, 52, p. 25, 1996.
Abate, et al. "Separation and Structural Characterization of Cyclic and Open Chain Oligomers Produced in Partial Pyrolysis of Microbial PHB's", *Macromolecules*, 28, p. 7911, 1995.
Alber, B., et al., "Malonyl-Coenzyme A Reductase in the Modified 3-Hydroxypropionate Cycle for Autotrophic Carbon Fixation in Archaeal *Metallosphaera* and *Sulfolobus* spp.", Journal of Bacteriology, 188(24):8551-8559 (2006).
Ariffin, H., et al., "Highly Selective Transformation of Poly[(R)-3-hydroxybutyric acid] into trans-Crotonic Acid by Catalytic Thermal Degradation", Polymer Degradation and Stability, 95:1375-1381 (2010).
Berg, et al., "Autotrophic Carbon Fixation in Archaea", Nat. Rev. Microbiol, ;:447 (2010).
Berg, et al. "A 3-Hydroxypropionate/4-Hydroxybutyrate Autotrophic Carbon Dioxide Assimilation Pathway in Archaea", Science, 318:1782 (2007).
Celinska, E., "Debottlenecking the 1,3-Propanediol Pathway by Metabolic Engineering", Biotechnology Advances, 28:519-530 (2010).
Coustou, V., et al., "A Mitochondrial NADH-dependent Fumarate Reductase Involved in the Production of Succinate Excreted by Procyclic Trypanosoma brucei", The Journal of Biological Chemistry, 280(17):16559-16570 (2005).
Dailly, Y., et al., "Novel Alcohol Dehydrogenase Activity in a Mutant of *Salmonella* Able to Use Ethanol as Sole Carbon Source", FEMS Microbiology Letters, 201:41-45 (2001).
Höfer, P., et al., "Introducing a New Bioengineered Bug. *Methylobacterium extorquens* Tuned as a Microbial Bioplastic Factory", Landes Bioscience, 2(2):71-79 (2011).
Kim, K.J., et al., "Thermal Degradation Behavior of Poly(4-hydroxybutyric acid)", Polymer Degradation and Stability, 91:2333-2341 (2006).
Kockelkorn, D. and Fuchs, G., "Malonic Semialdehyde Reductase, Succinic Semialdehyde Reductase, and Succinyl-Coenzyme A Reductase from *Metallosphaera sedula*: Enzymes of the Autotrophic 3-Hydroxybutyrate Cycle in *Sulfolobales*", Journal of Bacteriology, 191(20): 6352-6362 (2009).
Lin, H., et al., "Increasing the Acetyl-CoA Pool in the Presence of Overexpressed Phosphoenolpyruvate Carboxylase or Pyruvate Carboxylase Enhances Succinate Production in *Escherichia coli*", Biotechnol. Prog., 20:1599-1604 (2004).
Lu, Z., et al., "Evolution of an *Escherichia coli* Protein with Increased Resistance to Oxidative Stress", The Journal of Biological Chemistry, 273(14):8308-8316 (1998).
Panagiotou, G., et al., "Overexpression of a Novel Endogenous NADH Kinase in Aspergillus nidulans Enhances Growth", Metabolic Engineering, 11:31-39 (2009).
Rathnasingh, C., et al., "Production of 3-Hydroxypropionic Acid via Malonyl-CoA Pathway Using Recombinant *Escherichia coli* Strains", Journal of Biotechnology, 157:633-640 (2012).
Seo, M.-Y., et al., "Elimination of By-Product Formation During Production of 1,3-Propanediol in Klebsiella pneumoniae by Inactivation of Glycerol Oxidative Pathway", Applied Microbiological Biotechnology, 84:527-534 (2009).
Song, et al., "Construction of Recombinant *Escherichia coli* Strains Producing Poly(4-hydroxybutyric acid) Homopolyester From Glucose", Database Medline (online), U.S. National Library of Medicine, vol. 45, No. 3:382-386 (Jun. 2005).
Tong, I.-T., et al., "1,3-Propanediol Production by *Escherichia coli* Expressing Genes from the Klebsiella pneumoniae dha Regulon", Applied and Environmental Microbiology, 57(12):3541-3546 (1991).
Wang, Y, et al., "Construction of Recombinant *Bacillus subtilis* for Production of Polyhydroxyalkanoates", Applied Biochemistry and Biotechnology, 129-132: 1015-1022 (2006).
Wolf, M., et al., "Genes Encoding Xylan and β-glucan Hydrolysing Enzymes in Bacillus subtilis: Characterization, Mapping and Construction of Strains Deficient in Lichenase, Cellulase and Xylanase", Microbiology, 141:281-290 (1995).
WPI database, Week 200317, Thomson Scientific, London, GB; abstract of JP 2002 255952 A Sep. 11, 2002.
Yim, H., et al., "Metabolic Engineering of *Escherichia coli* for Direct Production of 1,4-Butanediol", Nature Chemical Biology, 7(7):445-452 (2011).
Zarzycki, et al., Identifying the Missing Steps of the Autotrophic 3-Hydroxypropionate $CO_2$ Fixation Cycle in *Chloroflexus aurantiacus*, PNAS, 106: 21317 (2009).
Notification of Transmittal of the International Search Report and The Written Opinion of The International Searching Authority for PCT/US2011/024612, "Process for Making Gamma Butyrolactone"; dated Jul. 1, 2011.
Notification Concerning Transmitall of International Preliminary Report on Patentability for PCT/US2011/024612, "Process for Making Gamma Butyrolactone"; dated Aug. 23, 2012.
Notification of Transmittal of the International Search Report and The Written Opinion of The International Searching Authority for PCT/US2012/035217, "Green Process for Producing Polyhydroxyalkanoates and Chemicals Using a Renewable Feedstock"; dated Dec. 4, 2012.
Notification Concerning Transmitall of International Preliminary Report on Patentability for PCT/US2012/035217, "Green Process for Producing Polyhydroxyalkanoates and Chemicals Using a Renewable Feedstock"; dated Nov. 7, 2013.
Notification of Transmittal of the International Search Report and The Written Opinion of The International Searching Authority for PCT/US2012/041512, "Biorefinery Process for THF Production"; dated Oct. 16, 2012.
Notification Concerning Transmitall of International Preliminary Report on Patentability for PCT/US2012/041512, "Biorefinery Process for THF Production"; dated Dec. 27, 2013.
Notification of Transmittal of the International Search Report and The Written Opinion of The International Searching Authority for PCT/US2012/050337, "Post Process Purification for Gamma-Butyrolactone Production"; dated Dec. 4, 2012.
Notification Concerning Transmitall of International Preliminary Report on Patentability for PCT/US2012/050337, "Post Process Purification for Gamma-Butyrolactone Production"; dated Feb. 20, 2014.
Notification of Transmittal of the International Search Report and The Written Opinion of The International Searching Authority for PCT/US2013/028913, "Genetically Engineered Microorganisms for the Production of Poly-4-Hydroxybutyrate"; dated Aug. 8, 2013.
Notification Concerning Transmitall of International Preliminary Report on Patentability for PCT/US2013/028913, "Genetically Engineered Microorganisms for the Production of Poly-4-Hydroxybutyrate"; dated Oct. 2, 2014.
Notification of Transmittal of the International Search Report and The Written Opinion of The International Searching Authority for PCT/US2013/044671, "Renewable Acrylic Acid Production and Products Made Therefrom"; dated Aug. 29, 2013.
Notification Concerning Transmitall of International Preliminary Report on Patentability for PCT/US2013/044671, "Renewable Acrylic Acid Production and Products Made Therefrom"; dated Dec. 18, 2014.

(56) References Cited

OTHER PUBLICATIONS

Invitation to Pay Additonal Fees and Partial International Search for PCT/US2014/016122, "Process for Ultra-Pure Chemical Production From Biobased Raw Starting Materials"; dated Jul. 10, 2014.
International Search Report for PCT/US2014/016122, "Process for Ultra-Pure Chemical Production From Biobased Raw Starting Materials"; dated Nov. 13, 2014.
Invitation to Pay Additional Fees and Partial International Search for PCT/US2014/044706, "Genetically Engineered Methylotrophs for the Production of PHA Biopolymers and C3, C4, and C5 Biochemicals From Methanol or Methane As Sole Carbon Feedstock"; dated Nov. 5, 2014.
International Search Report for PCT/US2014/044706, "Genetically Engineered Methylotrophs for the Production of PHA Biopolymers and C3, C4, and C5 Biochemicals From Methanol or Methane As Sole Carbon Feedstock"; dated Feb. 2, 2015.
Written Opinion for PCT/US2014/044706, "Genetically Engineered Methylotrophs for the Production of PHA Biopolymers and C3, C4, and C5 Biochemicals From Methanol or Methane As Sole Carbon Feedstock", dated Feb. 16, 2015.
Notice of Allowance for U.S. Appl. No. 13/578,214, "Process for Gamma-Butyrolactone Production"; dated Feb. 2, 2015.
Notice of Allowance for U.S. Appl. No. 13/578,214, "Process for Gamma-Butyrolactone Production"; dated Dec. 11, 2014.
Non Final Office Action for U.S. Appl. No. 13/578,214, "Process for Gamma-Butyrolactone Production"; dated May 30, 2014.
Zhang, L., et al., "Microbial production of 4-hydroxybutyrate, poly-4-hydroxybutyrate, and poly (3-hydroxybutyrate-co-4-hydroxybutyrate) by recombinant microorganisms," 2 Applied Microbiology and Biotechnology, 84:909-916 (2009).
Ex Parte Quayle Action for U.S. Appl. No. 14/406,491, "Renewable Acrylic Acid Production and Products Made Therefrom," dated Mar. 9, 2017.
Final Rejection for U.S. Appl. No. 10/326,442, "Methods of Making Intermediates from Polyhydroxyalkanoates," dated Aug. 20, 2004.
Final Rejection for U.S. Appl. No. 11/098,227, "Methods of Making Intermediates from Polyhydroxyalkanoates," dated Apr. 17, 2006.
Final Rejection for U.S. Appl. No. 14/386,728, "Genetically Engineered Microorganisms for the Production of Poly-4-Hydroxybutyrate," dated Jun. 1, 2016.
Non-Final Rejection for U.S. Appl. No. 10/326,442, "Methods of Making Intermediates from Polyhydroxyalkanoates," dated Jan. 28, 2004.
Non-Final Rejection for U.S. Appl. No. 11/098,227, "Methods of Making Intermediates from Polyhydroxyalkanoates," dated Aug. 30, 2005.
Non-Final Rejection for U.S. Appl. No. 12/497,362, "Single Solvent Polymer Extraction Methods," dated Nov. 12, 2009.
Non-Final Rejection for U.S. Appl. No. 13/793,707, "Process for Making Chemical Derivatives," dated Aug. 10, 2015.
Non-Final Rejection for U.S. Appl. No. 14/237,808, "Post Process Purification for Gamma-Butyrolactone Production," dated Apr. 4, 2016.
Non-Final Rejection for U.S. Appl. No. 14/386,728, "Genetically Engineered Microorganisms for the Production of Poly-4-Hydroxybutyrate," dated Sep. 4, 2015.
Non-Final Rejection for U.S. Appl. No. 14/386,728, "Genetically Engineered Microorganisms for the Production of Poly-4-Hydroxybutyrate," dated Sep. 8, 2017.
Non-Final Rejection for U.S. Appl. No. 14/767,509, "Process for Ultra Pure Chemical Production from Biobased Raw Starting Materials," dated Aug. 16, 2017.
Notice of Allowance for U.S. Appl. No. 10/326,442, "Methods of Making Intermediates from Polyhydroxyalkanoates," dated Jan. 1, 2005.
Notice of Allowance for U.S. Appl. No. 11/098,227, "Methods of Making Intermediates from Polyhydroxyalkanoates," dated Aug. 21, 2006.
Notice of Allowance for U.S. Appl. No. 12/497,362, "Single Solvent Polymer Extraction Methods," dated Aug. 5, 2010.
Notice of Allowance for U.S. Appl. No. 12/497,362, "Single Solvent Polymer Extraction Methods," dated Jul. 15, 2010.
Notice of Allowance for U.S. Appl. No. 12/497,362, "Single Solvent Polymer Extraction Methods," dated May 14, 2010.
Notice of Allowance for U.S. Appl. No. 14/406,491 dated Aug. 17, 2017.
Requirement for Restriction/Election for U.S. Appl. No. 13/793,707, "Process for Making Chemical Derivatives," dated Mar. 11, 2015.
Requirement for Restriction/Election for U.S. Appl. No. 14/125,045, "Biorefinery Process for THF Production," dated Feb. 2, 2015.
Requirement for Restriction/Election for U.S. Appl. No. 14/237,808, "Post Process Purification for Gamma-Butyrolactone Production," dated Oct. 8, 2015.
Requirement for Restriction/Election for U.S. Appl. No. 14/406,491, "Renewable Acrylic Acid Production and Products Made Therefrom," dated Jun. 7, 2016.
Bohmert et al., "Transgenic *Arabidopsis* Plants Can Accumulate Polyhydroxybutyrate to Up to 4% of Their Fresh Weight," Planta, 211: 841-845 (2000).
Braunegg et al., "A Tapid Gas Chromatographic Method for the Determination of Poly-Beta-hydroxybutyric Acid in Microbial Biomass," Eur J Applied Microbiology and Biotechnology, 6(1): 29-37 (1978).
Byrom, "Miscellaneous Biomaterials," Biomaterials, MacMillan Publishers, London, pp. 333-359 (1991).
Clarke et al., "Waterborne Coatings and Additives," editors D.R. Kara and W.D. Davies, The Royal Society of Chemistry, Publication No. 195: 18 (1995).
Comeau et al., "Determination of Poly-Beta-Hydroxybutyrate and Poly-Beta-Hydroxyvalerate in Activated Sludge by Gas-Liquid Chromatography," Applied and Enviromental Microbiology, 54(9): 2325-2327 (1988).
Grassie et al., "The Thermal Degradation of Poly(-(D)-Beta-Hydroxybutyric Acid): Part 1—Identification and Quantitative Analysis of Products," Polymer Degradation and Stability, 6: 47-61 (1984).
Hakkarainen et al., "Aliphatic Polyesters: Abiotic and Biotic Degradation and Degradation Products," Adv Polymer Sci, 157: 113-138 (2002).
Hocking et al., "Biopolyesters," Chemistry and Technology of Biodegradable Polymers, 48-96 (Chapman & Hall, London 1994).
Holmes, "Biologically Produced (R)-3-hydroxy-alkanoate Polymers and Copolymers," Developments in Crystalline Polymers, 2: 1-65 (1988).
Huijberts et al., "Gas-Chromatographic Analysis of Poly(3-Hydroxyalkanoates) in Bacteria," Biotechnology Techniques, 8(3): 187-192 (1994).
International Preliminary Report on Patentability for International Application No. PCT/US2014/016122 dated Aug. 18, 2015.
Jan et al., "Study of Parameters Affecting Poly(3-Hydroxybutyrate) Quantification by Gas Chromatography," Analytical Biochemistry, 225: 258-263 (1995).
Kunioka et al., Thermal Degradation of Microbial Copolyesters: Poly(3-hydroxybutyrate-co-3-hydroxyvalerate) and Poly(3-hydroxybutyrate-co-4-hydroxybutyrate), Macromolecules, 23(7): 1933-1936 (1990).
Lee et al., "Production of Poly(3-Hydroxybutyrate-co-3-Hydroxyhexanoate) by High-Cell-Density Cultivation of Aeromons Hydrophila," Biotechnology and Bioengineering, 67: 240-244 (2000).
Lehrle et al., Thermal Degradation of Bacterial Poly(hydroxybutyric acid): Mechanisms from the Dependence of Pyrolysis Yields on Sample Thickness, Macromolecules, 27(14): 372-3789 (1994).
Li et al., "Microbial Cell Factories for Production of Polyhydroxyalk Anoates," Chinese Journal of Biotechnology, 26(10): 1426-1435 (2010).
Matsusaki et al., "Biosynthesis and Properties of Poly(3-hydroxybutyrate-co-3-hydroxyalkanoates) by Recombinant Strains of *Pseudomonas* sp. 61-3," Biomacromolecules, 1: 17-22 (2000).
Mitomo et al., Thermal Decomposition of Poly(J-hydroxybutyrate) and its Copolmyer, Sen'I Gakkaishi,A118 47(2): 89-94 (1991).
Mitomo, "Aminolysis of Poly (Beta-Hydroxybutyrate) and its Copolymer," Sen-1-Gakkaishi, 48(11): 595-601 (1992).

(56) References Cited

OTHER PUBLICATIONS

Mohammadikhah et al., "Thermal Degradation and Kinetic Analysis of Pure Polyglycolic Acid in Presence of Humid Air," Iran Polym J, 17(9): 691-701 (2008).
Morikawa et al., "Pyrolysis of Bacterial Polyalkanoates," Canadian Journal of Chemistry, 59(15): 2306-2313 (1981).
Muller et al., "Poly(hydroxyalkanoates): A Fifth Class of Physiologically Important Organic Biopolymers?" Angewandte Chemie, 32(3): 477-502 (1993).
Nawrath et al., "Targeting of the Polyhydroxybutyrate Biosynthetic Pathway to the Plastids of *Arabidopsis thaliana* Results in High Levels of Polymer Accumulation," Proceedings of the National Academy of Sciences, 91(26): 12760-12764 (1994).
Park et al., "Production of Poly(3-hydroxybutyrate-co-3-hydroxyhexanoate) by Metabolically Engineered *Escherichia coli* Strains," Biomacromolecules, 2(1): 248-254 (2001).
Riis et al., "Gas Chromatographic Determination of Poly-betahydroxybutyric Acid in Microbial Biomass After Hydrochloric Acid Propanolysis," Journal of Chromatography, 445: 285-289 (1988).
Seebach et al., "Direct Degradation of the Biopolymer Poly[(R)-3-Hydroxybutyric Acid] to (R)-3-Hydroxybutanoic Acid and its Methyl Ester," Organic Synthesis, 39-41.
Steinbuchel, "Polyhydroxyalkanoic Acids," Biomaterials, MacMillan Publishers, London, pp. 123-213 (1991).
Valentin et al., "PHA Production, from Bacteria to Plans," International Journal of Macromolecules, 25: 303-306 (1999).
Veech et al., "Ketone Bodies, Potential Therapeutic Uses," IUMB Life, 51: 241-247 (2001).
Williams et al., "Biodegradable Plastics from Plants," Chemtech, 26: 38-44 (1996).
Xanthos et al., "Solvolysis," Frontiers in the Science and Technology of Polymer Recyclings, 425-436 (1998).
Zhang et al., "The Tricarboxylic Acid Cycle in Cyanobacteria," Science, 334: 1551-1553 (2011).
Zhu et al., "Cell Growth and By-Product Formation in a Pyruvate Kinase Mutatnt of *E. coli*," Biotechnol Prog, 17(4): 624-628 (2001).

\* cited by examiner

Propylene and Acrylate Sections

PROCESS FOR PRODUCING A MONOMER COMPONENT FROM A GENETICALLY MODIFIED POLYHYDROXYALKANOATE BIOMASS

This application is the U.S. National Stage of International Application No. PCT/US2011/024620, filed Feb. 11, 2011, which designates the U.S., published in English, and claims the benefit of U.S. Provisional Application No. 61/303,584, filed Feb. 11, 2010, U.S. Provisional Application No. 61/382,855, filed Sep. 14, 2010, and U.S. Provisional Application No. 61/413,195, filed Nov. 12, 2010. The entire teachings of the above applications are incorporated herein by reference.

BACKGROUND OF THE INVENTION

Biobased, biodegradable polymers such as polyhydroxyalkanoates (PHAs), are naturally produced in biomass systems, such as plant biomass, microbial biomass (e.g., bacteria including cyanobacteria, yeast, fungi) or algae biomass. Genetically-modified biomass systems have recently been developed which produce a wide variety of biodegradable PHA polymers and copolymers (Lee (1996), *Biotechnology & Bioengineering* 49:1-14; Braunegg et al. (1998), *J. Biotechnology* 65:127-161; Madison, L. L. and Huisman, G. W. (1999), Metabolic Engineering of Poly-3-Hydroxyalkanoates; From DNA to Plastic, in: *Microbiol. Mol. Biol. Rev.* 63:21-53).

There has also recently been progress in the development of biomass systems that produce "green" chemicals such as 1,3-propanediol (Dupont's BioPDO®), 1,4-butanediol (Genomatica) and succinic acid (Bioamber) to name a few. Analogous to the biobased PHA polymers, these biobased chemicals have been produced by genetically-modified biomass systems which utilize renewable feedstocks, have lower carbon footprints and reportedly lower production costs as compared to the traditional petroleum chemical production methods. However, one disadvantage of directly producing chemicals via a bioprocess is that the chemicals are often toxic to the cells that produce them so that the overall chemical yield from the cells is low. Also, other compounds produced by the cells end up as impurities in the chemicals of interest and, therefore, a purification step needs to be added to the process, adding an additional cost factor. Thus, a need exists to overcome the disadvantages of cell toxicity and purity described above.

SUMMARY OF THE INVENTION

It has been found that biobased chemicals (monomer components and derivatives) can be produced simply and cost effectively by thermal decomposition of genetically engineered biomass containing polyhydroxyalkanoates (PHA's) in the presence of a catalyst. Hosts can be genetically engineered to produce polyhydroxyalkanoates in their cells at enriched quantities and compositions. With the variety of PHA polymers available, a broad range of useful and important chemicals are produced easily and cheaply while overcoming the problems of cell toxicity and purity. The PHA polymers in the biomass are degraded to monomer components and other modified chemicals (e.g., derivatives) under conditions that are cost and time efficient.

The invention generally relates to methods for producing high purity, high yield, biobased monomer components from renewable carbon resources. The advantages of this biorefinery process are that it uses a renewable carbon source as the feedstock material, the genetically engineered hosts produce PHAs in high yield without adverse toxicity effects to the host cell (which could limit process efficiency) and when combined with catalysts and heated is capable of producing biobased monomer components and their derivatives in high yield with high purity.

In certain embodiments, the invention relates to methods of producing a monomer component from a genetically modified polyhydroxyalkanoate (PHA) biomass, comprising: heating the biomass in the presence of a catalyst to release a monomer component from the PHA, wherein the monomer component yield is about 70% based on one gram of monomer per gram of polyhydroxyalkanoate.

In certain embodiments, the polyhydroxyalkanoate is one or more selected from a polyglycolide, a poly-3-hydroxypropionate, a poly-3-hydroxybutyrate, a poly-4-hydroxybutyrate, a poly-5-hydroxyvalerate, or a co-polymer thereof. In some embodiments, the monomer component is glycolide, 3-hydroxypropriolactone, acrylic acid, crotonic acid, 5-hydroxyvalerolactone, or a mixture of any two or more thereof. In some embodiments, the monomer component contains less than 10% by weight side products. In certain embodiments, the biomass is from a recombinant host selected from a plant crop, bacteria, a yeast, a fungi, an algae, a cyanobacteria, or a mixture of any two or more thereof. In certain embodiments, the host is bacterial. In some embodiments, the bacteria is selected from *Escherichia coli, Alcaligenes eutrophus* (renamed as *Ralstonia eutropha*), *Bacillus* spp., *Alcaligenes latus, Azotobacter, Aeromonas, Comamonas, Pseudomonads, Pseudomonas, Ralstonia, Klebsiella*), *Synechococcus* sp PCC7002, *Synechococcus* sp. PCC 7942, *Synechocystis* sp. PCC 6803, *Thermosynechococcus elongatus* BP-I, *Chlorobium tepidum Chloroflexus auranticus, Chromatium tepidum, Chromatium vinosum Rhodospirillum rubrum, Rhodobacter capsulatus*, and *Rhodopseudomonas palustris*. In other embodiments, the host is a plant crop. In some embodiments, the plant crop is selected from tobacco, sugarcane, corn, switchgrass, miscanthus sorghum, sweet sorghum, or a mixture of any two or more thereof. In other embodiments, the host is a recombinant algae selected from *Chlorella minutissima, Chlorella emersonii, Chlorella sorokiniana, Chlorella ellipsoidea, Chlorella* sp., or *Chlorella protothecoides*. In certain embodiments, the genetically modified biomass has an increased amount of PHA production compared to wild-type organism.

In certain embodiments of the methods described herein, heating includes pyrolysis, torrefaction or flash pyrolysis. In some embodiments, the heating is at a temperature from about 200° C. to about 350° C. In other embodiments, the biomass is dried prior to heating. In still other embodiments, the drying is at a temperature of 100° C. to 175° C. In certain embodiments, the dried biomass has a water content of 5 wt %, or less. In certain embodiments, the heating is for about 1 minute to about 30 minutes or from 1 about minute to about 2 minutes.

In certain embodiments, the methods further comprising recovering the monomer component, for example condensing or other recovery methods.

In other embodiments, the catalyst is a metal catalyst or an organic catalyst. In some embodiments, the catalyst by weight is 4% to 15%.

In another aspect, methods of the invention include drying a biomass (e.g., genetically engineered biomass), comprising PHA, heating the dried biomass at 200-350° C. to produce monomer components and then modifying the monomer products by direct hydrogenation, esterification and/or amidation to produce the corresponding diols, hydroxyl esters or amides. For example, when a biomass comprises poly-3HB, the monomer component, crotonic acid, can be further modified to other four carbon products (C4 products, e.g., derivatives) including but not limited to fumaric acid, butene, maleic anhydride (MAN), 2-propylene, acrylic acid and the like. Likewise, when a biomass comprises 3-hydroxypropionate (3HP), the monomer component, β-propiolactone, can be modified to other three carbon products (C3 products, e.g. derivatives) such as acrylic acid, methyl acrylate, acrylamide, acrylonitrile, ethyl 3-hydroxypropioate, malonic acid and the like. Biomass comprising poly 5-hydroxyvalerate to produce δ-valerolactone can also be modified to other five carbon (C5) products (e.g., derivatives).

In some embodiments, methods of producing crotonic acid from a genetically modified polyhydroxyalkanoate (PHA) biomass are described. These methods include heating the biomass in the presence of a catalyst to release crotonic acid component from the PHA, wherein the monomer yield is about 70% based on one gram of monomer per gram of polyhydroxyalkanoate, reacting the crotonic acid forming a lower alkyl crotonate ester; and reacting the lower alkyl (e.g., butyl) crotonate ester under suitable conditions to form a lower alkyl acrylate and a butene via cross-metathesis in the presence of a first catalyst with a sufficient amount of propylene. The propylene can be formed from a metathesis reaction of ethylene and 2-butene in the presence of a second catalyst and excess propylene is continuously removed. The lower alkyl crotonate ester can further be reacted presence of a second catalyst to form an alcohol.

In certain aspects, the first catalyst is a metathesis catalyst (e.g., a Hoveyda-Grubb's cross metathesis catalyst, 1,3-bis (2,4,6-trimethylphenyl)-2-imidazolidinylidene)dichloro(o-isopropoxyphenylmethylene)ruthenium or the like). In other aspects, the first catalyst is not exposed to ethylene. In certain aspects, the second catalyst is a metathesis catalyst.

In other embodiments, methods of producing crotonic acid from a genetically modified polyhydroxyalkanoate (PHA) biomass include heating the biomass in the presence of a catalyst to release a crotonic acid component from the PHA, wherein the crotonic acid component yield is about 70% based on one gram of monomer per gram of polyhydroxyalkanoate reacting the crotonic acid to form a butyl crotonate ester, and hydrogenating the butyl crotonate ester to form two moles of butanol. In certain embodiments, the methods include producing a 3-hydroxypropriolactone from a genetically modified polyhydroxyalkanoate (PHA) biomass, comprising heating the biomass in the presence of a catalyst e.g., sodium carbonate or ferrous sulfate heptahydrate to release a monomer component from the PHA, wherein the monomer component yield is about 70% based on one gram of monomer component per gram of polyhydroxyalkanoate and acrylic acid is formed. In some embodiments, methods of producing crotonic acid from a genetically modified polyhydroxyalkanoate (PHA) biomass are provided, comprising heating the biomass in the presence of a catalyst to release crotonic acid component from the PHA, wherein the monomer yield is about 70% based on one gram of monomer per gram of polyhydroxyalkanoate and the crotonic acid is further modified to fumaric acid, butene, maleic anhydride (MAN), 2-propylene, or acrylic acid.

In some embodiments, the catalyst is metal catalyst. In certain embodiments, the catalyst is a chloride, oxide, hydroxide, nitrate, phosphate, sulphonate, carbonate or stearate compound containing a metal ion that is aluminum, antimony, barium, bismuth, cadmium, calcium, cerium, chromium, cobalt, copper, gallium, iron, lanthanum, lead, lithium, magnesium, molybdenum, nickel, palladium, potassium, silver, sodium, strontium, tin, tungsten, vanadium or zinc or mixtures thereof. In some embodiments, the catalyst is an organic catalyst that is an amine, azide, enol, glycol, quaternary ammonium salt, phenoxide, cyanate, thiocyanate, dialkyl amide and alkyl thiolate or mixtures thereof. In certain embodiments, the catalyst is calcium hydroxide, ferrous sulfate heptahydrate, or sodium carbonate or mixture of these. In certain embodiments, the catalyst is a fixed catalyst bed consisting of ⅛ alumina granules impregnated with vanadium pentoxide or similar compounds.

In another aspect, the invention further pertains to a continuous biorefinery process for production of acrylic acid from a PHA biomass using a multiple tandem catalysis reaction protocol, comprising: culturing a genetically engineered PHA biomass to produce poly-3-hydroxybutyrate, pyrolyzing the poly-3 hydroxybutyrate to produce crotonic acid, reacting the crotonic acid to form a lower alkyl crotonate ester in the presence of a transesterification catalyst; and reacting the lower alkyl crotonate ester under suitable conditions to form a lower alkyl acrylate and a butene via cross-metathesis in the presence of a first metathesis catalyst with a sufficient amount of propylene, wherein the propylene is formed from a metathesis reaction of ethylene and 2-butene in the presence of a second metathesis catalyst and excess propylene is continuously removed.

In another embodiment, the invention pertains to a continuous biorefinery process for the production of acrylic acid from a genetically engineered PHA biomass comprising, culturing the genetically engineered PHA biomass to produce poly-3-hydroxypropionate, heating the poly-3-hydroxypropionate with a catalyst to produce acrylic acid, and recovering the acrylic acid. In yet another embodiment, the invention related to a continuous biorefinery process for the production of glycolide from a genetically engineered PHA biomass comprising, culturing the genetically engineered PHA biomass to produce polyglycolide heating the polyglycolide with a catalyst to produce a glycolide monomer component, and recovering the glycolide monomer. A continuous biorefinery process for the production of 5-hydroxyvalerolactone from a genetically engineered PHA biomass comprising, culturing the genetically engineered PHA biomass to produce poly-5-hydroxyvalerolactone, heating the poly-5-hydroxyvalerolactone with a catalyst to produce a 5-hydroxyvalerolactone monomer, and recovering the 5-hydroxyvalerolactone monomer.

In the continuous biorefinery processes, the culturing is continuous, and the other steps in each described embodiment (e.g., heating, reacting etc) are continuous performed according to standard manufacturing procedures.

In certain embodiments, the recovering of the monomer component includes condensing the monomer component. As used herein, the term "recovering" as it applies to the monomer component means to isolate it from the biomass materials, for example including but not limited to: recovering by condensation, separation methodologies, such as the use of membranes, gas (e.g., vapor) phase separation, such as distillation, and the like. Thus, the recovering may be accomplished via a condensation mechanism that captures the monomer component vapor, condenses the monomer component vapor to a liquid form and transfers it away from the biomass materials.

In another aspect, a process is provided including drying switch grass leaves (e.g., genetically engineered switch grass leaves), including poly-3-hydroxyproprionate at a temperature of 100° C. to 175° C. to provide a dried switch leaves having a water content of 5 wt %, or less; heating the dried switch grass leaves to a temperature of from 200° C. to 350° C. for a time period sufficient to decompose the poly-3-hydroxyproprionate and release acrylic acid, and produce a residual biomass; recovering the acrylic acid; and torrefying the residual biomass. In some embodiments, the time period is from 1 minute to 5 minutes. In other embodiments, the time period is from 1 minute to 2 minutes. In some embodiments, the recovering the acrylic acid includes condensing the acrylic acid. In some embodiments, torrefying includes maintaining a temperature of the residual biomass at 200° C. to 350° C. In certain embodiments, the torrefying includes maintaining the temperature for a time period of 10 minutes to 30 minutes. In some embodiments, the processes described also includes adding a catalyst to the biomass prior to heating. In certain embodiments, the catalyst is metal catalyst.

In another aspect, a process is provided including drying tobacco leaves (e.g., genetically engineered tobacco leaves), including poly-3-hydroxybutyrate at a temperature of 100° C. to 175° C. to provide dried tobacco leaves having a water content of 5 wt %, or less; heating the dried tobacco leaves to a temperature of from 200° C. to 350° C. for a time period sufficient to decompose the poly-3-hydroxybutyrate and release a mixture of cis- and trans-crotonic acid, and produce a residual biomass; recovering the cis- and trans-crotonic acid; and torrefying the residual biomass. In some embodiments, the time period is from 1 minute to 10 minutes or from 1 minute to 5 minutes or from 1 minute to 2 minutes or time periods between these times. In some embodiments, the recovering the cis- and trans-crotonic acid includes condensing the cis- and trans-crotonic acid. In some embodiments, the torrefying includes maintaining a temperature of the residual biomass at 200° C. to 350° C. In some embodiments, the torrefying includes maintaining the temperature for a time period of 10 minutes to 30 minutes (or time periods between these times). In some embodiments, the process also includes adding a catalyst to the biomass prior to heating. In certain embodiments, the catalyst is metal catalyst.

In another aspect, a process is provided including treating a biomass (e.g., genetically engineered biomass), including a PHA in a lignocellulosic process to produce fermentable sugars; drying the biomass to provide a dried biomass having a water content of 5 wt %, or less; heating the biomass to a temperature of from 200° C. to 350° C. for a time period sufficient to decompose the PHA and release a monomer component, and produce a residual biomass; recovering the monomer component and using the residual biomass as a fuel. In some embodiments, the process further includes recovering the fermentable sugars. In some embodiments, the process also includes adding a catalyst to the biomass prior to heating. In certain embodiments, the catalyst is metal catalyst.

PHA biomass has been genetically modified to increase the yield of PHA over wild-type biomass, the biomass is then treated to produce versatile intermediates that can be further processed to yield desired commodity and specialty products.

In certain embodiments, the production of the biomass uses multiple tandem catalysis reactions. The utilization of renewable raw materials from PHA biomass for generating desirable products, e.g., acrylic acids conforms to the principles of green technology without the disadvantages of utilizing petroleum feedstocks.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1:
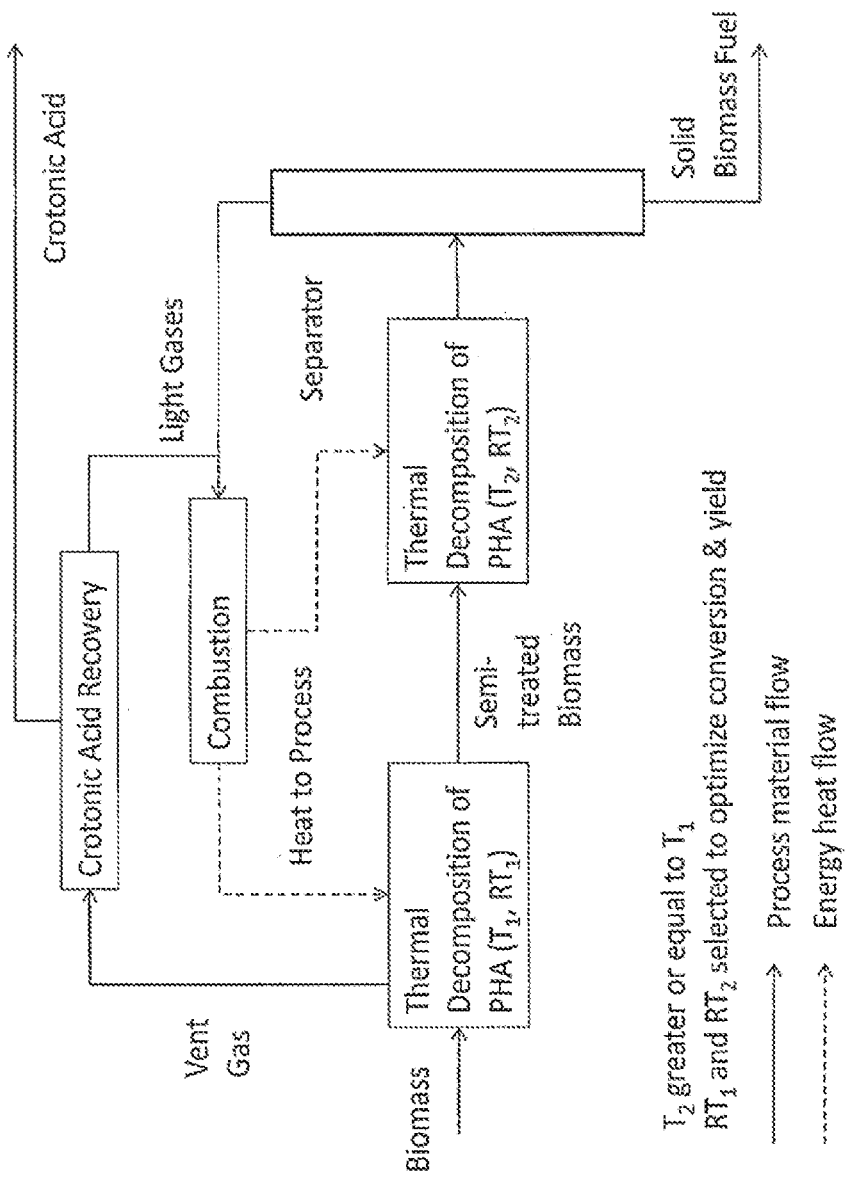
FIG. 1 is a schematic of PHA recovery from biomass with residual converted to solid fuel, according to various embodiments.

A description of example embodiments of the invention follows.

In general, the invention pertains to the production of commodity and specialty chemicals from genetically engineered polyhydroxyalkanoate polymer biomasses under controlled conditions. Described herein are methods for obtaining chemical products from PHA containing biomass. In one aspect, the biomass has been genetically engineered to produce PHA that is at a higher concentration or amount than the PHA that naturally occurs in the wild-type biomass. The host organism has been genetically modified by introduction of genes and/or deletion of genes in a wild-type or genetically engineered PHA producer creating strains that synthesize PHA from inexpensive feedstocks. The PHA biomass is produced in a fermentation process where the genetically engineered microbe is fed a renewable substrate. Renewable substrates include fermentation feedstocks such as sugars, vegetable oils, fatty acids or synthesis gas produced from plant crop material. The level of PHA produced in the biomass from the sugar substrate is greater than 10% (for example, 15%, 20%, 25%, 30%, 35%, 40%, 45%, 50%, 55%, 60%, 65%, 70%, 75% or 80%). The enrichment of the PHA allows for direct increases of starting PHA products and conversion to monomer components for further processing into other reaction products. In another embodiment, the biomass has been genetically engineered to produce a PHA with certain monomer components. In certain aspects, these monomer components, are intermediates for further processing to other reaction products or monomer components for example, monomer components that are commodity chemicals.

In another aspect, a method is provided for converting a PHA in a dried PHA-containing biomass (e.g., genetically engineered biomass) to monomer components, such as lactones, glycolides, and organic acids that are recovered as commodity chemicals and used in other processes or reactions. In certain embodiments, this process is integrated with a torrefaction process by which the residual biomass continues to be thermally treated once the volatile chemical intermediates have been released to provide a fuel material. Fuel materials produced by this process are used for direct combustion or further treated to produce pyrolysis liquids or syngas. Overall, the process has the added advantage that the residual biomass is converted to a higher value fuel which can then be used for the production of electricity and steam to provide energy for the process thereby eliminating the need for waste treatment.

Although it is known that polyhydroxyalkanoates (PHAs) are thermally unstable in their pure form, it was surprisingly found that when PHAs are present in biomass in an unpurified form, they may be converted to small molecule chemical intermediates, i.e. monomer components having from 3 to 6 carbon atoms, in high yield (e.g., at about 70%, about 80%, about 85%, about 90%, about 95%) and surprisingly high purity (e.g., from about 95% to about 100%). By heating the biomass to a predetermined temperature for a short period of time, the conversion of the PHA to the chemical intermediates may be effected. The monomer components are then recovered and their value exploited. However, a significant amount of a residual biomass remains from the process. As used herein, the term "residual biomass" refers to the biomass after PHA conversion to the small molecule intermediates. The residual biomass may then be converted via torrefaction to a useable, fuel, thereby reducing the waste from PHA production and gaining additional valuable commodity chemicals from typical torrefaction processes. As noted above, the torrefaction is conducted at a temperature that is sufficient to densify the residual biomass.

In the present technology, it has been found that when the torrefaction temperature is maintained for a short period of time (e.g., at time period between 1-5 minutes) monomer components of a PHA contained within the biomass may be collected in high yield and purity. Thus, in some embodiments, after drying of the biomass to form a dried biomass, the dried biomass is heated to a temperature between about 200° C. to about 350° C. for a short period of time. In some embodiments, the short time period is from 1 minute to 5 minutes. In other embodiments, the short time period is from 1 minute to 2 minutes, or less than one minute (e.g., 55 seconds, 50 seconds, 45 seconds, 40 seconds, or less) or from 1 minute to 4 minutes or from 2 minutes to 5 minutes, or from 3 minutes to 5 minutes or from 2 minutes to 5 minutes, or in some embodiments 5 minutes to 10 minutes. The temperature is at a temperature of about 200° C. to about 350° C. and includes temperatures between, for example, about 205° C., about 210° C., about 220° C., about 230° C., about 240° C., about 250° C., about 260° C., about 270° C., about 280° C., about 290° C., about 300° C., about 310° C., about 320° C., about 330° C., about 340° C., about 345° C., as well as temperatures between these temperatures.

These surprising observations allow for a temporal separation of fast PHA conversion at a temperature of, at or between about 200° C. to about 350° C. to produce the monomer components followed by slow torrefaction at about 200° C. to about 350° C. to produce a solid fuel. Thus, the monomer components are recovered and their value exploited and the biomass may be converted to valuable solid fuels which are recovered.

Alternatively, it has also been found that the biomass (e.g., genetically engineered biomass) containing the PHA, may be first dried and the PHA converted to the monomer components in a fast, high-temperature, flash pyrolysis with the monomer components being recovered, and the residual biomass subjected high temperatures for conversion into solid fuels. The fast, high-temperature, flash pyrolysis is conducted at temperatures greater than 500° C. (for example, about 510° C., about 520° C., about 530° C., about 540° C., about 550° C., about 560° C., about 570° C., about 580° C., about 590° C., about 600° C., about 610° C., about 620° C., about 630° C., about 640° C., about 650° C., about 660° C., about 670° C., about 680° C., about 690° C., about 700° C., about 710° C., about 720° C., about 730° C., about 740° C., about 750° C., about 760° C., about 770° C., about 780° C., about 790° C., about 800° C., or greater than about 800° C.) with a residence time sufficient to decompose at least a portion of the biomass into pyrolysis liquids and a pyrolyzed biomass. In some embodiments, the residence time is from 1 second to 15 seconds, or from 5 seconds to 20 seconds. In other embodiments, the residence times are from 1 second to 5 seconds, or less than 5 sec. The temperature and time can be optimized for each product or monomer component. Other products from the flash pyrolysis process include other light gases that may be collected and recovered, or may be burned as fuel, providing process steam and/or heat for the entire process.

A process for recovering PHA-based chemical intermediates from biomass is schematically outlined in FIG. 1, as a non-limiting flow chart process. FIG. 1 describes an integrated PHA recovery system from a biomass with residual biomass converted to fuels.

According to some embodiments, PHAs are those that will provide a series of monomer components that can be readily recovered at low cost, and energy efficiently, without the prior separation of the PHA from the biomass. Suitable PHA materials are those that formed by the intracellular polymerization of one or more monomer components. Suitable monomer components of the PHAs include, but are not limited to, 3-hydroxybutyrate, 3-hydroxypropionate, 3-hydroxyvalerate, 3-hydroxyhexanoate, 3-hydroxyheptanoate, 3-hydroxyoctanoate, 3-hydroxynonanoate, 3-hydroxydecanoate, 3-hydroxydodecanoate, 3-hydroxydodecenoate, 4-hydroxybutyrate, 4-hydroxyvalerate, 5-hydroxyvalerate, and 6-hydroxyhexanoate. Such monomer components may form homopolymers or co-polymers.

In some embodiments, the PHA is a homopolymer. As used herein, the term "homopolymer" refers to a polymer in which there is a single monomer component present in the polymer. Examples of PHA homopolymers include, but are not limited to, poly-3-hydroxypropionate (poly-3HP), poly-3-hydroxybutyrate (poly 3-HB), poly-4-hydroxybutyrate (poly 4-HB), poly 5-hydroxypentanoate, poly-6-hydroxyhexanoate, polylactic acid, and polyglycolic acid.

In other embodiments, the PHA is a co-polymer. As used herein, the term "co-polymer" refers to a polymer which contains two, or more, different monomer components. Examples of PHA copolymers include poly-3-hydroxybutyrate-co-3-hydroxypropionate, poly-3-hydroxybutyrate-co-(D)-lactide, poly-3-hydroxybutyrate-co-4-hydroxybutyrate (poly-3HB-co-4HB), poly-3-hydroxybutyrate-co-3-hydroxyvalerate (poly-3-HB-co-3HV), poly-3-hydroxybutyrate-co-5-hydroxyvalerate, and poly-3-hydroxybutyrate-co-3-hydroxyhexanoate. In some embodiments, where the PHA is a copolymer, the ratio of the first co-monomer to the second co-monomer can be from 3% to 97% on a weight basis. Although examples of PHA copolymers having two different monomer components have been provided, the PHA can have more than two different monomer components (e.g., three different monomer components, four different monomer components, five different monomer components etc.).

The monomer components that are recovered from the PHA conversion are unique to each particular PHA polymer. Degradation reactions typically favor either β-elimination to produce an unsaturated alkenoic acid, or de-polymerization to form lactones corresponding to the reverse of a ring-opening polymerization. Typical thermal decomposition reactions are shown below as several, non-limiting examples:

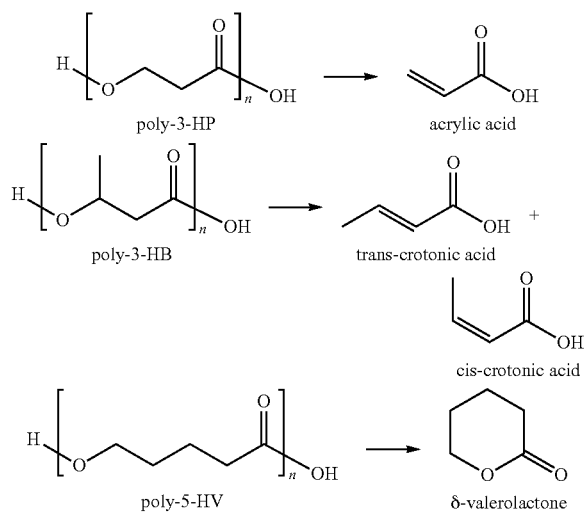

The unsaturated alkenoic acids and lactones can then be further converted (e.g., modified) by conventional catalytic means to produce additional derivative products.

Thus, according to one embodiment, a process is provided including drying microbial or plant, biomass that contains a suitable level of a PHA; optionally adding a suitable catalyst; drying the biomass to form a dried biomass having a low moisture content; heating the dried biomass to a temperature range of between about 200° C. to about 350° C. for a period of about 1-5 minutes. This results in controlled decomposition of the PHA to the monomer components as a vapor phase that may then be recovered via condensation. After the PHA is decomposed, the residual biomass may then be fed to a torrefaction reactor operating at a temperature of about 200° C. to about 350° C. (or a temperature in between these temperatures, such as those described herein) with a residence time of between about 10 to about 30 min to produce a torrefied biomass and residual light (fuel) gases. Non-condensable gases from the decomposition of the PHA, are to be fed to the torrefaction reactor for recovery as fuel.

According to another embodiment, after the PHA is decomposed as described above, the residual biomass is fed to a high-temperature, flash pyrolysis reactor that typically operates a temperature of about 500° C., or greater, with residence time of 1 second to 15 seconds to produce condensable liquid pyrolysis oils and light non-condensable gases that are recovered for fuel, and a charred biomass that may also be used as a solid fuel. In some embodiments, the excess heat from the high-temperature, flash pyrolysis is used to heat the lower temperature PHA decomposition reactor. Such integration of all stages in one process can result in high overall energy efficiency for the process.

According to another embodiment, a PHA-containing biomass is treated by standard lignocellulosic processes to produce fermentable sugars and a lignin-rich fraction of the biomass. Such lignocellulosic processes utilize dilute acids and enzymatic treatment of the biomass. Because various PHAs are typically resistant to dilute acid and enzymatic treatment, the PHAs largely remain in the residual biomass after such treatment. As is typical in lignocellulosic facilities, the residual lignin-rich biomass is dried to be used as fuel. However, according the embodiment, prior to feeding the lignin-rich biomass to a power or steam generating plant, the PHA is recovered by thermal decomposition of about 200° C. to about 350° C. (or a temperature in between these temperatures, such as those described herein) with a residence time of about 1-5 minutes (or less, or a resident time between these times, such as those described herein), yielding the corresponding PHA monomer components, and a second reduced lignin-rich biomass. The reduced lignin-rich biomass from the reactor can then be fed directly to boilers, or, alternatively, further processed to yield torrefied biomass or pyrolysis oils. Such heat integration may be used with power or steam generation plants that use biomass fuels and are possible using standard engineering techniques of process integration.

In previous embodiments, the conversion of PHAs to corresponding chemicals of interest by low temperature degradation was described. For example, poly-3HP can be converted directly to acrylic acid via thermolysis using a different catalyst.

In another embodiment, it is also possible to subject the PHA chemicals generated from thermolysis directly to hydrogenation, esterification or amidation conditions to produce the corresponding diols, hydroxyl esters and amides. For instance poly-3HB yields butanol or maleic anhydride when subjected to hydrogenation with $H_2$ or oxidation respectively. A significant problem with direct conversion of biomass containing PHA via chemical means is the potential for side reactions with biomass lipids, sugars and proteins wasting expensive reagents and resulting in poor selectivity and purity. New reactor configurations will however need to be developed to handle the biomass feedstocks as opposed to conventional liquid or gaseous feedstocks. It would therefore be of significant benefit to first isolate the PHA as a small molecule that can then be converted to a variety of downstream chemicals using conventional hydrogenation, esterification and amidation catalysts and reactors.

The processing of fats and oils to produce alcohols provides some guidance in this respect. Oils and fats are significant sources of fatty alcohols that are used in a variety of applications such as lubricants and surfactants. The fats are not typically hydrogenated directly as the intensive reaction conditions tend to downgrade the glycerol to lower alcohols such as propylene glycol and propanol during the course of the hydrogenation. For this reason it is more conventional to first hydrolyze the oil and then pre-purify the fatty acids to enable a more efficient hydrogenation (see for instance Lurgi's hydrogenation process in Bailey's Industrial Oil and Fat Products, Sixth Edition, Six Volume Set. Edited by Fereidoon Shahidi, John Wiley & Sons, Inc. 2005).

Poly-3HB (Poly-3-hydroxybutyrate) is the simplest PHA found in nature and is converted to crotonic acid when subjected to thermolysis at 250-350° C. During this reaction various isomers are formed that are not readily separated (trans, cis and iso-crotonic acid). Crotonic acid has some specialty uses but is not a major chemical feedstock. In fact, crotonaldehyde was historically produced (via aldol condensation of acetaldehyde) as the primary feedstock for butanol production. Only minor quantities of crotonaldehyde were converted to crotonic acid despite being a straightforward conversion.

By using a highly selective conversion of poly-3HB to crotonic acid, it is possible to separate and purify the poly-3HB content contained in biomass of microbial or plant origin using direct thermolysis to crotonic acid. In a modification of the classic crotonaldehyde to butanol process the crotonic acid is reduced to butanol via direct hydrogenation. Alternatively, the crotonic acid can be esterified first and then hydrogenated to release the corresponding alcohols.

Compared to the decarboxylation process, the hydrogenation step proceeds with the loss of water only and 86% of the crotonic molecular weight is preserved in the butanol. Butanol is a versatile and important chemical feedstock. One use of butanol is for the production of butyl acrylate (butanol and acrylic acid esterification) that is used widely in the architectural coatings. Combining biomass based poly-3HP conversion to acrylic acid and biomass based poly-3HB conversion to crotonic acid followed by hydrogenation to butanol will yield 100% renewable feedstock based precursors allowing production of fully renewable butyl acrylate.

Many different techniques have been developed to hydrogenate fatty acids with Bailey's Industrial Oil and Fat products providing a good overview. Several patents describe various different hydrogenation catalysts and processes (see U.S. Pat. Nos. 5,334,779, 4,480,115 and 6,495,730, incorporated by reference). Direct reduction of crotonic acid to butanol can also accomplished chemically as described in J. Org. Chem. 1981 46 (12).

Historically fatty acids have not been directly hydrogenated to corresponding alcohols as the acid has a tendency to degrade the catalyst employed. For this reason the acid is typically converted to an ester followed by hydrogenation, typically over a fixed bed. This process requires separation and recycling of alcohol and is therefore less efficient than direct hydrogenation. Different catalysts systems have been developed to allow direct hydrogenation of fatty acids in aqueous solution (e.g., Lurgi hydrogenation of maleic anhydride to butanediol). It is also possible to use a slurry process to hydrogenate the acid by feeding into a large recirculating stream of the alcohol product. Under the reaction conditions this results in in-situ esterification, thereby protecting the catalysts. Advantageously, any double bonds are simultaneously reduced as well.

In certain embodiments, a monomer component is modified or converted to other monomer components. For example, crotonic acid is further modified or converted to other monomer components such as maleic anhydride. For example, crotonic acid has limited markets but is a very versatile building block chemical. Conversion of crotonic acid to butanol via crotonaldehyde and also conversion to propylene via decarboxylation are modification routes as well as oxidation of crotonic acid to form maleic anhydride. Maleic anhydride is a functional chemical building block with applications in unsaturated polyester resins, as a starting material for butanediol and also diverse applications in plasticizers, agrochemicals and as a starting material for fumaric and maleic acids.

Maleic anhydride is typically produced via catalytic partial oxidation of butane. Several commercial processes are in use including fixed bed technology and fluid bed technology processes. Maleic anhydride is recovered and purified via a solvent or aqueous process. Melt crystallization processes have also been developed to produce high purity maleic anhydride after initial separation via distillation. Melt crystallization processes are also disclosed to produce high purity maleic anhydride after initial separation. U.S. Pat. No. 5,929,255 discloses a melt precipitation process to co-produce and purify both maleic anhydride and fumaric acid to avoid losses associated with incineration of fumaric acid that is co-produced with maleic anhydride during oxidation of butane. The direct production of maleic acid from crotonic acid as provided herein, offers several advantages over the conventional process of butane oxidation. Compared to the butane oxidation process that has a heat of formation $\Delta Hf=-1236$ kJ/mol the direct partial oxidation of crotonic acid has a $\Delta Hf=-504$ kJ/mol. The process therefore generates less co-product steam that represents a yield loss and also requires co-location of butane plants with big steam users such as a refinery.

Recombinant Hosts with Metabolic Pathways for Producing PHA

Genetic engineering of hosts (e.g., bacteria, fungi, algae, plants and the like) as production platforms for modified and new materials provides a sustainable solution for high value industrial applications for production of chemicals. Described herein are process methods of producing monomer components and other modified chemicals from a genetically modified recombinant polyhydroxyalkanoate (PHA) biomass. The processes described herein avoid toxic effects to the host organism by producing the biobased chemical post culture or post harvesting, are cost effective and highly efficient (e.g., use less energy to make), decrease greenhouse emissions, use renewable resources and can be further processed to produce high purity products in high yield.

As used herein, "PHA biomass" is intended to mean any genetically engineered biomass that includes a non-naturally occurring amount of polyhydroxyalkanoate polymer (PHA). The wild-type PHA biomass refers to the amount of PHA that an organism typically produces in nature. In certain embodiments, the biomass titer (g/L) of PHA has been increased when compared to the host without the overexpression or inhibition of one or more genes in the PHA pathway. In certain embodiments, the PHA titer is reported as a percent dry cell weight (% wdc) or as grams of PHA/Kg biomass. In some embodiments, a source of the PHA biomass is a plant crop, bacteria, yeast, fungi, algae, cyanobacteria, or a mixture of any two or more thereof.

"Overexpression" refers to the expression of a polypeptide or protein encoded by a DNA introduced into a host cell, wherein the polypeptide or protein is either not normally present in the host cell, or where the polypeptide or protein is present in the host cell at a higher level than that normally expressed from the endogenous gene encoding the polypeptide or protein. "Inhibition" or "down regulation" refers to the suppression or deletion of a gene that encodes a polypeptide or protein. In some embodiments, inhibition means inactivating the gene that produces an enzyme in the pathway. In certain embodiments, the genes introduced are from a heterologous organism.

Genetically engineered microbial PHA production systems with fast growing organisms such as *Escherichia coli* have been developed. Genetic engineering allows for the modification of wild-type microbes to improve the production of specific PHA copolymers or to introduce the capability to produce different PHA polymers by adding PHA biosynthetic enzymes having different substrate-specificity or even kinetic properties to the natural system. Examples of these types of systems are described in Steinbuchel & Valentin, *FEMS Microbiol. Lett.* 128:219-28 (1995). PCT Publication No. WO 1998/04713 describes methods for controlling the molecular weight using genetic engineering to control the level of the PHA synthase enzyme. Commercially useful strains, including *Alcaligenes eutrophus* (renamed as *Ralstonia eutropha*), *Alcaligenes latus, Azotobacter vinlandii*, and *Pseudomonads*, for producing PHAs are disclosed in Lee, *Biotechnology & Bioengineering*, 49:1-14 (1996) and Braunegg et al., (1998), *J. Biotechnology* 65: 127-161. In some embodiments, a source of the biomass includes the bacteria, *E. coli*. The *E. coli* may be one which has been genetically engineered to express or overexpress one or more PHAs. Exemplary strains, fermentation, media and feed conditions are described in U.S. Pat. Nos. 6,316,262; 6,323,010; 6,689,589; 7,081,357; 7,202,064 and 7,229,804.

Recombinant host containing the necessary genes that will encode the enzymatic pathway for the conversion of a carbon substance to PHA may be constructed using techniques known in the art.

The following general approach is used for generating transgenic *E. coli* PHB producers: (1) a promoterless antibiotic resistance (abr) gene is cloned in the polylinker of a suitable plasmid such as pUC18NotI or pUC18SfiI so that the major part of the polylinker is upstream of abr; (2) phb genes are subsequently cloned upstream of and in the same orientation as the abr gene; (3) the phb-abr cassette is excised as a NotI or AvrII fragment (AvrII recognizes the SfiI site in pUC18SfiI) and cloned in the corresponding sites of any plasmid like those from the pUT- or pLOF-series; (4) the resulting plasmids are maintained in *E. coli* A strains and electroporated or conjugated into the *E. coli* strain of choice in which these plasmids do not replicate; and (5) new strains in which the phb-abr cassette has successfully integrated in the chromosome are selected on selective medium for the host (e.g., naladixic acid when the host is naladixic acid resistant) and for the cassette (e.g., chloramphenicol, kanamycin, tetracyclin, mercury chloride, bialaphos). The resulting PHB integrants are screened on minimal medium in the presence of glucose for growth and PHB formation. Modifications of this general procedure can be made. Recombinant hosts containing the necessary genes that will encode the enzymatic pathway for the conversion of a carbon substrate to PHA may be constructed using techniques well known in the art.

For example, for the production of acrylic acid monomer, a genetically engineered host that produces P3HP is needed. For the production of poly 3HP, recombinant host such as those described in U.S. Pat. Nos. 6,576,450, 6,316,262; 6,323,010; 6,689,589; 7,081,357; 7,202,064 and 7,229,804 can be used. In general, if a host organism does not naturally produce PHA, genes for the P3PH pathway can be introduced. For example, to produce the 3HP polymers directly from carbohydrate feedstocks, host can be further engineered to express glycerol-3-phosphate dehydrogenase and glycerol-3-phosphatase. Such recombinant *E. coli* strains and methods for their construction are known in the art (Anton, D. "Biological production of 1,3-propanediol", presented at United Engineering Foundation Metabolic Engineering II conference, Elmau, Germany, Oct. 27, 1998; PCT WO 1998/21339).

Recombinant hosts for producing polyhydroxyalkanoates (PHAs) comprising 5-hydroxy valerate (5HV) monomers and methods of producing PHAs comprising 5HV monomers from renewable carbon substrates are described in WO 2010/068953 A2. A recombinant host expressing genes encoding a polyhydroxyalkanoate (PHA) synthase and a 5-hydroxyvalerate-CoA (5HV-CoA) transferase or 5HV-CoA synthetase and at least one transgene encoding a heterologous enzyme involved in lysine catabolic pathways wherein the host produces a PHA polymer containing 5HV monomers when the organism is provided with a renewable carbon substrate selected from: lysine, starch, sucrose, glucose, lactose, fructose, xylose, maltose, arabinose or combinations thereof and the level of 5HV monomer produced is higher than in the absence of expression of the transgene(s) are provided. An exemplary host for production of poly 5-hydroxyvalerate expresses one or more genes encoding lysine 2-monooxygenase, 5-aminopentanamidase, 5-aminopentanoate transaminase, glutarate semialdehyde reductase, 5-hydroxy valerate CoA-transferase, and polyhydroxyalkanoate synthase to produce a PHA polymer containing 5HV monomers. Certain hosts have deletions or mutations in genes encoding glutarate semialdehyde dehydrogenase and/or lysine exporter encoding genes.

Also described are hosts with one or more of the genes encoding PHA synthase, 5HV-CoA transferase or 5HV-CoA synthetase is also expressed from a transgene to produce the poly-5-hydroxyvalerate polymers that can be used in the methods described herein.

Also hosts that naturally produce PHAs can be used and further manipulated to increase PHA yields. Examples of such organisms include *Ralstonia eutropha, Alcaligenes latus* and *Azotobacter* but many others are well-known to those skilled in the art (Braunegg et al. 1998, *Journal of Biotechnology* 65: 127-161). The introduction of the diol dehydratase is accomplished using standard techniques as described by Peoples and Sinskey (1989, *J. Biol. Chem.* 164, 15298-15303). Genetically engineered host can then be used select for increased resistance to 3-hydroxypropionaldehyde. In other embodiments, mutations that are beneficial for the production of the P3HP homopolymers in these organisms can also be utilized. For example, specific mutations include inactivating the β-ketothiolase and/or acetoacetyl-CoA reductase genes. As these genes are generally well known and available or isolatable, gene disruptions can be readily carried out as described for example by Slater et. al., 1998 (*J. Bacteriol.*) 180(8): 1979-87.

Acrylic acid, also known as 2-propenoic acid is intended to mean the carboxylic acid having the chemical formula $C_3H_4O_2$. Acrylic acid is a clear, colorless liquid that is soluble in water and is fully miscible in alcohols, ethers, and chloroform. Acrylic acid is the simplest unsaturated carboxylic acid with both a double bond and a carbonyl group. Acrylic acid includes the acrylate ion and salts. As used herein, "acrylate ester" refers the ester form of acrylic acid.

Methods of obtaining desired genes from a source organism (host) are common and well known in the art of molecular biology. Such methods can be found described in, for example, Sambrook et al., *Molecular Cloning: A Laboratory Manual*, Third Ed., Cold Spring Harbor Laboratory, New York (2001); Ausubel et al., *Current Protocols in Molecular Biology*, John Wiley and Sons, Baltimore, Md. (1999). For example, if the sequence of the gene is known, the DNA may be amplified from genomic DNA using polymerase chain reaction (Mullis, U.S. Pat. No. 4,683,202) with primers specific to the gene of interest to obtain amounts of DNA suitable for ligation into appropriate vectors. Alternatively, the gene of interest may be chemically synthesized de novo in order to take into consideration the codon bias of the host organism to enhance heterologous protein expression. Expression control sequences such as promoters and transcription terminators can be attached to a gene of interest via polymerase chain reaction using engineered primers containing such sequences. Another way is to introduce the isolated gene into a vector already containing the necessary control sequences in the proper order by restriction endonuclease digestion and ligation. One example of this latter approach is the BioBrick™ technology (see the world wide web at biobricks.org) where multiple pieces of DNA can be sequentially assembled together in a standardized way by using the same two restriction sites.

In addition to using vectors, genes that are necessary for the enzymatic conversion of a carbon substrate to PHA can be introduced into a host organism by integration into the chromosome using either a targeted or random approach. For targeted integration into a specific site on the chromosome, the method generally known as Red/ET recombineering is used as originally described by Datsenko and Wanner (*Proc. Natl. Acad. Sci. USA*, 2000, 97, 6640-6645). Random integration into the chromosome involved using a mini-Tn5 transposon-mediated approach as described by Huisman et al. (U.S. Pat. Nos. 6,316,262 and 6,593,116).

Strains have been developed to produce copolymers, a number of which have been produced in recombinant *E. coli*. These copolymers include poly(3-hydroxybutyrate-co-3-hydroxyvalerate) (PHBV), poly(3-hydroxybutyrate-co-4-hydroxybutyrate) (P3HB-co-4HB), poly(4-hydroxybutyrate) (P4HB) and long side chain PHAs comprising 3-hydroxyoctanoate units (Madison and Huisman, 1999. Strains of *E. coli* containing the phb genes on a plasmid have been developed to produce P(3HB-3HV) (Slater, et al., *Appl. Environ. Microbiol.* 58:1089-94 (1992); Fidler & Dennis, *FEMS Microbiol Rev.* 103:231-36 (1992); Rhie & Dennis, Appl. *Environ. Microbiol.* 61:2487-92 (1995); Zhang, H. et al., *Appl. Environ. Microbiol.* 60:1198-205 (1994)). The production of P(4HB) and P(3HB-4HB) in *E. coli* is achieved by introducing genes from a metabolically unrelated pathway into a P(3HB) producer (Hein, et al., *FEMS Microbiol. Lett.* 153:411-18 (1997); Valentin & Dennis, *J. Biotechnol.* 58:33-38 (1997)). *E. coli* also has been engineered to produce medium short chain polyhydroxyalkanoates (msc-PHAs) by introducing the phaC1 and phaC2 gene of *P. aeruginosa* in a fadB::kan mutant (Langenbach, et al., *FEMS Microbiol. Lett.* 150:303-09 (1997); Qi, et al., *FEMS Microbiol. Lett.* 157:155-62 (1997)).

Methods for production of plants have been described in U.S. Pat. No. 5,245,023 and U.S. Pat. Nos. 5,250,430; 5,502,273; 5,534,432; 5,602,321; 5,610,041; 5,650,555: 5,663,063; and PCT Publication Nos.: WO 1991/00917, WO 1992/19747, WO 1993/02187, WO 1993/02194 and WO 1994/12014, Poirier et. al., 1992, *Science* 256; 520-523, Williams and Peoples, 1996. *Chemtech* 26, 38-44, the teachings of which are incorporated by reference herein).

Transgenic plants, in particular, transplastomic plants, have been developed that produce increased levels of polyhydroxyalkanoates (PHAs). Methods and constructs for genetically engineering plant plastids with genes for high level, stable PHA, in particular PHB, production are described. See for example, PCT Publication No.: WO 2010/102220, incorporated by reference herein. Proof of concept studies for polyhydroxybutyrate (PHB) synthesis in switchgrass (Somleva et al., *Plant Biotechnol. J.* 6:663-678 (2008)), sugarcane (Petrasovits et al., *Plant Biotechnol. J.* 5:162-172 (2007); Purnell et al., *Plant Biotechnol. J.* 5:173-184 (2007)), canola (Valentin et al., *Int. J. Biol. Macromol.* 25:303-306 (1999); Slater et al., *Nat. Biotechnol.* 17:1011-1016 (1999); Houmiel et al., *Planta* 209:547-550 (1999)), and corn stover (Poirier et al., 2002, Polyhydroxyalkanoate production in transgenic plants, in Biopolymers, Vol 3a, Steinbuchel, A. (ed), Wiley-VHC Verlag GmbH, pgs 401-435), have been reported. While these studies have yielded significant scientific results (Slater et al., *Nat. Biotechnol.* 17:1011-1016 (1999)), higher yields that enhance overall economics of polymer produced in a crop platform are needed. The weight percent PHA in the wild-type biomass varies with respect to the source of the biomass. For microbial systems produced by a fermentation process from renewable resource-based feedstocks such as sugars, vegetable oils or glycerol, the amount of PHA in the biomass may be about 65 wt %, or more, of the total weight of the biomass. For plant crop systems, in particular biomass crops such as sugarcane or switchgrass, the amount of PHA may be about 3%, or more, of the total weight of the biomass. For algae or cyanobacterial systems, the amount of PHA may be about 40%, or more of the total weight of the biomass.

U.S. Patent Application: US20100229258, incorporated herein by reference, describes fertile transgenic plants producing elevated levels of PHAs, i.e., at least 10% dry weight in plant tissues and, were produced using plastid-encoded gene expression In certain aspects of the invention, the recombinant host has been genetically engineered to produce an increased amount of PHA as compared to the wild-type host. For example, in certain embodiments, the PHA is increased between about 20% to about 90% over the wild-type or between about 50% to about 80%. In other embodiments, the recombinant host produces at least about a 20% increase of PHA over wild-type, at least about a 30% increase over wild-type, at least about a 40% increase over wild-type, at least about a 50% increase over wild-type, at least about a 60% increase over wild-type, at least about a 70% increase over wild-type, at least about a 75% increase over wild-type, at least about a 80% increase over wild-type or at least about a 90% increase over wild-type. In other embodiments, the PHA is between about a 2 fold increase to about a 400 fold increase over the amount produced by the wild-type host. The amount of PHA in the host or plant is determined by gas chromatography according to procedures described in Doi, *Microbial Polyesters*, John Wiley&Sons, p24, 1990. In certain embodiments, a biomass titer of 100-120 g PHA/Kg of biomass is achieved. In other embodiments, the amount of PHA titer is presented as percent dry cell weight (% dcw).

In some embodiments, the PHA is polyglycolide, poly-3-hydroxypropionate, poly-3-hydroxybutyrate, poly-4-hydroxybutyrate, poly-5-hydroxybutyrate, or a co-polymer thereof. In certain embodiments, the PHA is polyglycolide, poly-3-hydroxypropionate, poly-3-hydroxybutyrate, poly-4-hydroxybutyrate, or poly-5-hydroxybutyrate. In certain embodiments, the PHA is poly-3-hydroxybutyrate. In other embodiments, the PHA is poly-3-hydroxypropionate.

In certain embodiments, it may be desirable to label the constituents of the biomass. For example, it may be useful to deliberately label with an isotope of carbon (e.g., $^{13}C$) to facilitate structure determination or for other means. This is achieved by growing microorganisms genetically engineered to express the constituents, e.g., polymers, but instead of the usual media, the bacteria are grown on a growth medium with $^{13}C$-containing carbon source, such as glucose, glycerol, pyruvic acid, etc. In this way polymers can be produced that are labeled with $^{13}C$ uniformly, partially, or at specific sites. Additionally, labeling allows the exact percentage in bioplastics that came from renewable sources (e.g., plant derivatives) can be known via ASTM D6866—an industrial application of radiocarbon dating. ASTM D6866 measures the Carbon 14 content of biobased materials; and since fossil-based materials no longer have Carbon 14, ASTM D6866 can effectively dispel inaccurate claims of biobased content Culturing of Host to Produce PHA Biomass In general, the recombinant host is cultured in a medium with a carbon source and other essential nutrients to produce the PHA biomass by fermentation techniques either in batches or continuously using methods known in the art. Additional additives can also be included, for example, anti foam agents and the like for achieving desired growth conditions. Fermentation is particularly useful for large scale production. An exemplary method uses bioreactors for culturing and processing the fermentation broth to the desired product. Other techniques such as separation techniques can be combined with fermentation for large scale and/or continuous production.

As used herein, the term "feedstock" refers to a substance used as a carbon raw material in an industrial process. When used in reference to a culture of organisms such as microbial or algae organisms such as a fermentation process with cells, the term refers to the raw material used to supply a carbon or other energy source for the cells. Carbon sources useful for the production of monomer components include simple, inexpensive sources, for example, glucose, sucrose, lactose, fructose, xylose, maltose, arabinose and the like. In other embodiments, the feedstock is molasses or starch, fatty acids, vegetable oils or a lignocelluloses material and the like. It is also possible to use organisms to produce the PHA biomass that grow on synthesis gas ($CO_2$, CO and hydrogen) to produced from renewable biomass resourses.

Introduction of PHA pathway genes allows for flexibility in utilizing readily available and inexpensive feedstocks. As used herein, the term "feedstock" refers to a substance used as a raw material in an industrial process. When used in reference to a culture of microbial or algae organisms such as a fermentation process with cells, the term refers to the raw material used to supply a carbon or other energy source for the cells. A "renewable" feedstock refers to a renewable energy source such as material derived from living organisms or their metabolic byproducts including material derived from biomass, often consisting of underutilized components like chaff or stover. Agricultural products specifically grown for use as renewable feedstocks include, for example, corn, soybeans, switchgrass and trees such as poplar, wheat, flaxseed and rapeseed, sugar cane and palm oil. As renewable sources of energy and raw materials, agricultural feedstocks based on crops are the ultimate replacement of declining oil reserves. Plants use solar energy and carbon dioxide to make thousands of complex and functional biochemicals beyond the capability of the modern synthetic chemistry. These include fine and bulk chemicals, pharmaceuticals, polymers, resins, food additives, bio-colorants, adhesives, solvents, and lubricants.

In general, during or following production (e.g., culturing) of the PHA biomass, the biomass is combined with a catalyst to convert the PHA polymer to high purity monomer component product. The catalyst (in solid or solution form) and biomass are combined for example by mixing, flocculation, centrifuging or spray drying, or other suitable method known in the art for promoting the interaction of the biomass and catalyst driving an efficient and specific conversion of PHB to monomer component. In some embodiments, the biomass is initially dried, for example at a temperature between about 100° C. and about 150° C. and for an amount of time to reduce the water content of the biomass. The dried biomass is then re-suspended in water prior to combining with the catalyst. Suitable temperatures and duration for drying are determined for product purity and yield and can in some embodiments include low temperatures for removing water (such as between 25° C. and 150° C.) for an extended period of time or in other embodiments can include drying at a high temperature (e.g., above 450° C.) for a short duration of time. Alternatively, the water can be removed by other methods known in the art other than heating. Under "suitable conditions" refers to conditions that promote the catalytic reaction. For example, under conditions that maximize the generation of the product monomer component such as in the presence of co-agents or other material that contributes to the reaction efficiency. Other suitable conditions include in the absence of impurities, such as metals or other materials that would hinder the reaction from progression.

Thermal Degradation of the PHA Biomass

"Heating," "pyrolysis", "thermolysis" and "torrefying" as used herein refer to thermal degradation (e.g., decomposition) of the PHA biomass for conversion to monomer components. In general, the thermal degradation of the PHA biomass occurs at an elevated temperature in the presence of a catalyst. For example, in certain embodiments, the heating temperature for the processes described herein is between about 200° C. to about 400° C. In some embodiments, the heating temperature is about 200° C. to about 350° C. In other embodiments, the heating temperature is about 300° C. "Pyrolysis" typically refers to a thermochemical decomposition of the biomass at elevated temperatures over a period of time. The duration can range from a few seconds to hours. In certain conditions, pyrolysis occurs in the absence of oxygen or in the presence of a limited amount of oxygen to avoid oxygenation. The processes for PHA biomass pyrolysis can include direct heat transfer or indirect heat transfer. "Flash pyrolysis" refers to quickly heating the biomass at a high temperature for fast decomposition of the PHA biomass, for example, depolymerization of a PHA in the biomass. Another example of flash pyrolysis is RTP™ rapid thermal pyrolysis. RTP™ technology and equipment from Envergent Technologies, Des Plaines, Ill. converts feedstocks into biooil. "Torrefying" refers to the process of torrefaction, which is an art-recognized term that refers to the drying of biomass. The process typically involves heating a biomass in a temperature range from about 200 to about 350° C., over a relatively long duration (e.g., 10-30 minutes), typically in the absence of oxygen. The process results for example, in a torrefied biomass having a water content that is less than 7 wt % of the biomass. The torrefied biomass may then be processed further. In some embodiments, the heating is done in a vacuum, at atmospheric pressure or under controlled pressure. In certain embodiments, the heating is accomplished without the use or with a reduced use of petroleum generated energy.

In certain embodiments, the PHA biomass is dried prior to heating. Alternatively, in other embodiments, drying is done during the thermal degradation (e.g., heating, pyrolysis or torrefaction) of the PHA biomass. Drying reduces the water content of the biomass. In certain embodiments, the biomass is dried at a temperature of between about 100° C. to about 350° C., for example, between about 200° C. and about 275° C. In some embodiments, the dried PHA biomass has a water content of 5 wt %, or less.

The heating of the PHA biomass/catalyst mixture is carried out for a sufficient time to efficiently and specifically convert the PHA biomass to monomer component. In certain embodiments, the time period for heating is from about 30 seconds to about 1minute, from about 30 seconds to about 1.5 minutes, from about 1 minute to about 10 minutes, from about 1 minute to about 5 minutes or a time between, for example, about 1 minute, about 2 minutes, about 1.5 minutes, about 2.5 minutes, about 3.5 minutes.

In other embodiments, the time period is from about 1 minute to about 2 minutes. In still other embodiments, the heating time duration is for a time between about 5 minutes and about 30 minutes, between about 30 minutes and about 2 hours, or between about 2 hours and about 10 hours or for greater that 10 hours (e.g., 24 hours).

In certain embodiments, the heating temperature is at a temperature of about 200° C. to about 350° C. including a temperature between, for example, about 205° C., about 210° C., about 215° C., about 220° C., about 225° C., about 230° C., about 235° C., about 240° C., about 245° C., about 250° C., about 255° C. about 260° C., about 270° C., about 275° C., about 280° C., about 290° C., about 300° C., about 310° C., about 320° C., about 330° C., about 340° C., or 345° C. In certain embodiments, the temperature is about 250° C. In certain embodiments, the temperature is about 275° C.

As used herein, "olefin metathesis" refers an organic reaction that entails redistribution of alkylene fragments by the scission of carbon-carbon double bonds in olefins (alkenes). Olefin metathesis advantages include the creation of fewer side products and hazardous wastes. The reaction proceeds via alkene double bond cleavage, followed by a statistical redistribution of alkylidene fragments. The reaction is catalyzed by metallorganic catalysts that include metals such as nickel, tungsten, rhenium, ruthenium and molybdenum. In comparison, molybdenum catalysts are typically more reactive toward olefins, although they also react with aldehydes and other polar or protic groups. Ruthenium reacts preferentially with carbon-carbon double bonds over most other species, which makes these catalysts unusually stable toward alcohols, amides, aldehydes, and carboxylic acids. Examples of catalysts include the Grubbs' catalysts (ruthenium carbine complexes) and Schrock alkylidenes catalysts (molybdenum(VI) and tungsten(VI)-based catalysts) discussed in more detail below. In the methods described herein, the olefin metathesis is cross metathesis.

As used herein, "catalyst" refers to a substance that initiates or accelerates a chemical reaction without itself being affected or consumed in the reaction. Examples of useful catalysts include metal catalysts. In certain embodiments, the catalyst lowers the temperature for initiation of thermal decomposition and increases the rate of thermal decomposition at certain pyrolysis temperatures (e.g., about 200° C. to about 325° C.).

According to some embodiments of any of the processes, the efficiency of the conversion and the selectivity for a particular intermediate chemical is promoted by the addition of a catalyst to the biomass before or during conversion. The catalyst is a material that will promote elimination reactions or co-hydroxyl unzipping reactions of the PHA polymer chains in the biomass. In certain embodiments, the catalyst is a metal catalyst. In some embodiments, the catalyst is a chloride, oxide, hydroxide, nitrate, phosphate, sulphonate, carbonate or stearate compound containing a metal ion that is aluminum, antimony, barium, bismuth, cadmium, calcium, cerium, chromium, cobalt, copper, gallium, iron, lanthanum, lead, lithium, magnesium, molybdenum, nickel, palladium, potassium, silver, sodium, strontium, tin, tungsten, vanadium or zinc. In some embodiments, the catalyst is an organic catalyst including but not limited to an amine, azide, enol, glycol, quaternary ammonium salt, phenoxide, cyanate, thiocyanate, dialkyl amide and alkyl thiolate. The amount of catalyst is an amount sufficient to promote the reaction. Mixtures of two or more catalysts are also included.

In certain embodiments, the amount of metal catalyst is about 0.1% to about 15% based on the weight of metal ion relative to the dry solid weight of the biomass. In some embodiments, the amount of catalyst is between about 7.5% and about 12%. In other embodiments, the amount of catalyst is about 0.5% dry cell weight, about 1%, about 2%, about 3%, about 4%, about 5%, about 6%, about 7%, about 8%, about 9%, about 10%, about 11%, about 12%, about 13%, about 14%, about 15%, or higher such as up to 20%, or higher such as up to 30%, or higher such as up to 40%, or higher such as up to 50%.

In certain embodiments, recovery of the catalyst is further included in the processes of the invention. For example, when a calcium catalyst is used calcination is a useful recovery technique. Calcination is a thermal treatment process that is carried out on minerals, metals or ores to change the materials through decarboxylation, dehydration, devolatilization of organic matter, phase transformation or oxidation. The process is normally carried out in reactors such as hearth furnaces, shaft furnaces, rotary kilns or more recently fluidized beds reactors. The calcination temperature is chosen to be below the melting point of the substrate but above its decomposition or phase transition temperature. Often this is taken as the temperature at which the Gibbs free energy of reaction is equal to zero. For the decomposition of $CaCO_3$ to CaO, the calcination temperature at $\Delta G=0$ is calculated to be ~850° C. Typically for most minerals, the calcination temperature is in the range of 800-1000° C.

To recover the calcium catalyst from the biomass after recovery of the monomer component, one would transfer the spent biomass residue directly from pyrolysis or torrefaction into a calcining reactor and continue heating the biomass residue in air to 825-850° C. for a period of time to remove all traces of the organic biomass. Once the organic biomass is removed, the catalyst could be used as is or purified further by separating the metal oxides present (from the fermentation media and catalyst) based on density using equipment known to those in the art.

As used herein, the term "sufficient amount" when used in reference to a chemical reagent in a reaction is intended to mean a quantity of the reference reagent that can meet the demands of the chemical reaction.

As used herein, "hydrogenation" means to treat with hydrogen, also a form of chemical reduction, is a chemical reaction between molecular hydrogen ($H_2$) and another compound or element, usually in the presence of a catalyst. The process is commonly employed to reduce or saturate organic compounds.

As used herein, "lower alkyl" refers to a C2-C4 alkyl, (e.g., ethyl, propyl butyl).

As used herein, lower alkene refers to a C2-C4 alkene, (e.g., ethene (ethylene), propylene, butene). "Ethylene" (ethene) is a colorless flammable gas that exhibits solubility in water. "Propylene" is an unsaturated organic compound having the chemical formula $C_3H_6$, "Butene", also known as butylene, is an alkene with the formula $C_4H_8$. It is a colourless gas that is present in crude oil as a minor constituent in quantities that are too small for viable extraction. It is therefore obtained by catalytic cracking of long chain hydrocarbons left during refining of crude oil. Cracking produces a mixture of products and the 2-butene is extracted from this by fractional distillation.

"Esterification", as used herein refers to the chemical reaction in which two reactants (typically an alcohol and an acid) form an ester as the reaction product.

A "carbon footprint" is a measure of the impact the processes have on the environment, and in particular climate change. It relates to the amount of greenhouse gases produced.

The present technology, thus generally described, will be understood more readily by reference to the following examples, which are provided by way of illustration and are not intended to be limiting of the present technology.

In certain embodiments, "recovering" the monomer vapor includes condensing the vapor. As used herein, the term "recovering" as it applies to the vapor means to isolate it from the PHA biomass materials, for example including but not limited to: recovering by condensation, separation methodologies, such as the use of membranes, gas (e.g., vapor) phase separation, such as distillation, and the like. Thus, the recovering may be accomplished via a condensation mechanism that captures the monomer component vapor, condenses the monomer component vapor to a liquid form and transfers it away from the biomass materials.

As a non-limiting example, the condensing of monomer component vapor may be described as follows. The incoming gas/vapor stream from the pyrolysis/torrefaction chamber enters an interchanger, where the gas/vapor stream may be pre-cooled. The gas/vapor stream then passes through a chiller where the temperature of the gas/vapor stream is lowered to that required to condense the designated vapors from the gas by indirect contact with a refrigerant. The gas and condensed vapors flow from the chiller into a separator, where the condensed vapors are collected in the bottom. The gas, free of the vapors, flows from the separator, passes through the Interchanger and exits the unit. The recovered liquids flow, or are pumped, from the bottom of the separator to storage. For some of the products, the condensed vapors solidify and the solid is collected.

In other embodiments, the monomer component can be further purified if needed by additional methods known in the art, for example, by distillation, by reactive distillation (e.g., the monomer component is acidified first to oxidize certain components (e.g., for ease of separation) and then distilled) by treatment with activated carbon for removal of color and/or odor bodies, by ion exchange treatment, by liquid-liquid extraction—with a monomer component immiscible solvent to remove fatty acids etc, for purification after monomer recovery, by vacuum distillation, by extraction distillation or using similar methods that would result in further purifying the monomer component to increase the yield of monomer. Combinations of these treatments can also be utilized.

In certain embodiments, the process is selective for producing monomers with a relatively small amount of undesired side products. The term "monomer component" of the process includes the monomer and side products, such as dimers and oligomers. In certain embodiments, the monomer component can include 95% by weight monomer such as acrylic acid and 5% side products such as dimers. Thus the amount of monomer in the monomer component can be about 70% by weight, about 71% by weight, about 72% by weight, about 73% by weight, about, 74% by weight, about 75% by weight, about 76% by weight, about 77% by weight, about 78% by weight, about 79% by weight, about 80% by weight, 81% by weight, about 82% by weight, about 83% by weight, about 84% by weight, about 85% by weight, about 86% by weight, about 87% by weight, about 88% by weight, about 89% by weight, about 90% by weight, 91% by weight, about 92% by weight, about 93% by weight, about 94% by weight, about 95% by weight, about 96% by weight, about 97% by weight, about 98% by weight, about 99% by weight, or about 100% by weight.

The use of a specific catalyst in a sufficient amount will reduce the production of undesired side products and increase the yield of monomer by at least about 2 fold. In some embodiments, the production of undesired side products will be reduced to at least about 50%, at least about 40%, at least about 30%, at least about 20% at least about 10%, or about at least about 5%. In certain embodiment, the undesired side products will be less than about 5% of the recovered monomer, less than about 4% of the recovered monomer, less than about 3% of the recovered monomer, less than about 2% of the recovered monomer, or less than about 1% of the recovered monomer.

The processes described herein can provide a yield of monomer component expressed as a percent yield, for example, when grown from glucose as a carbon source, the yield is up to 95% based on [gram PHA component per gram glucose]×100% or the yield of monomer is expressed as [gram monomer per gram of PHA component]×100%. In other embodiments, the yield is in a range between about 40% and about 95%, for example between about 50% and about 70%, or between about 60% and 70%. In other embodiment, the yield is about 75%, about 70%, about 65%, about 60%, about 55%, about 50%, about 45% or about 40%. Thus, the yield can be calculated ((g of monomer component/g of starting PHA)×100%)

Production of Crotonic Acid

Crotonic acid is a useful chemical intermediate that is commercially produced by the catalytic oxidation of crotonaldehyde. The size of the market for crotonic acid is currently estimated at $5 million. However, it is under utilized as a feedstock chemical intermediate because it can be catalytically converted to more value added chemicals like butanol, acrylic acid, maleic acid and fumaric acid that are building blocks for the production of adhesives, paints, coatings, personal care products and engineering resins.

New processes for converting "natural" olefin products to useful biobased chemicals have recently been reported (J. Metzger (2009), *Eur. J. Lipid Sci*, 111, p865; A. Ryback, M. Meier (2007), *Green Chem.*, 9, p1356; US2009/0155866A1, by M. Burk et al.). The key to these processes is the use of metathesis catalysts for reacting different types of olefins, of which the first well defined, highly active catalysts were developed by Schrock and Grubb and subsequently extended by Hoveyda (Y. Schrodt, R. Pederson (2007), *Aldrichimica* ACTA, vol. 40, no. 2, p 45).

Cross metathesis has become a particularly important reaction pathway for producing biobased chemicals from biomass feedstocks. For example, cross metathesis of plant-based unsaturated fatty acids with ethylene has the potential to sustainably produce a variety of polymers including polyesters, polyamides and polyethers in high yield (V. P. Kukhar (2009), *Kem. Ind.*, 58 (2), p57). Ethylene is a convenient monomer to react with other biobased compounds because it can lead directly to a range of high volume commodity intermediates like acrylic acids and esters. With the development of "green" ethylene, produced by catalytic dehydration of biobased ethanol (A. Morschbaker (2009), *Polymer Reviews*, vol. 49, Iss. 2, p79), the ability to produce 100% biobased intermediates is becoming an attractive option. One challenge, however, in reacting ethylene monomer with Grubbs catalysts is the propensity for the ethylene to deactivate or degrade the catalyst which leads to low rates of conversion and yield loss (Z. Lysenko et. al. (2006), *J. of Organometallic Chem.,* 691, p5197; X. Lin et. al. (2010), *J. of Molecular Catalysis A: Chemical,* 330, p99; K. Burdett et. al. (2004), *Organometallics,* 23, p2027). This is especially important when developing industrial applications using metathesis catalysts.

Described herein are methods that overcome this problem utilizing a multiple tandem catalysis reaction method and process. In the first stage, ethylene and 2-butene are first converted to propylene using a metathesis catalyst which is not sensitive to deactivation by ethylene such as Schrock's molybdenum-alkylidene or tungsten-alkylidene catalysts (Schrock et. al. (1988), *J. Am. Chem. Soc.,* 110, p1423). In the second stage, the propylene is then reacted with the desired biobased compound using a Grubb's catalyst (such as (1,3-bis(2,4,6-trimethylphenyl)-2-imidazolidinylidene) dichloro(o-isopropoxyphenylmethylene) ruthenium). In this reaction scheme, the Grubb's catalyst is never exposed to ethylene and is therefore able to maintain the high reaction rates and high yields needed for industrial biochemical processes.

In one aspect of the invention a continuous biorefinary process for production of acrylic acid from PHA biomass using a multiple tandem catalysis reaction protocol is described. The process includes growing a genetically engineered PHA biomass to produce poly-3-hydroxybutyrate, heating (e.g., flash pyrolyzing) the poly-3 hydroxybutyrate to produce crotonic acid, reacting the crotonic acid under suitable conditions to form a lower alkyl crotonate ester in the presence of a transesterification catalyst; reacting the lower alkyl crotonate ester under suitable conditions to form a lower alkyl acrylate and a butene via cross-metathesis in the presence of a first metathesis catalyst with a sufficient amount of propylene. The propylene is formed from a separate metathesis reaction of ethylene and 2-butene in the presence of a second metathesis catalyst and excess propylene is continuously removed.

As stated above, PHB is well known to be thermally unstable (Cornelissen et al, Pp. 2523-2532, *Fuel,* 87, 2008) and is converted under certain conditions to intermediates including crotonic acid upon heating (See Kopinke et al, *Polymer Degradation and Stability,* 52:25-38 (1996,). Crotonic acid can be further processed to acrylic acid and acrylate esters. Polymer thermal stability is typically a limiting factor for thermoplastic applications, however, as described herein can be leveraged to convert low cost PHB (e.g., from biomass sources) to crotonic acid at high purity and high yields. Crotonic acid itself has limited markets, mostly being used as a comonomer in vinyl systems where it imparts some hydrophobic properties to the final products. The crotonic acid is reacted under suitable conditions to form a lower alkyl crotonate ester, and reacting the lower alkyl crotonate ester under suitable conditions to form a lower alkyl acrylate and a butene via cross-metathesis in the presence of a first catalyst with a sufficient amount of proplylene.

The biobased chemicals produced from the biomass (e.g., crotonic acid, acrylic acid, propylene, butane etc.) can be utilized a starting materials for a wide variety of applications. For example, acrylic acid and its esters readily combine with themselves or other monomers (e.g. acrylamides, acrylonitrile, vinyl, styrene, and butadiene) by reacting at their double bond, forming homopolymers or copolymers which are used in the manufacture of various plastics, paper manufacture and coating, exterior house paints for wood and masonry, coatings for compressed board and related building materials, flocculation of mineral ore fines and waste water, and treatment of sewage, printing inks, interior wall paints, floor polishes, floor and wall coverings, industrial primers, textile sizing, treatment and finishing, leather impregnation and finishing and masonry sealers, coatings, adhesives, elastomers, as well as floor polishes, and paints. Acrylic acid is also used in the production of polymeric materials such polyacrylic acid, which is a major component of superabsorbant diapers.

Likewise, propylene is raw material for a wide variety of products including polypropylene, a versatile polymer used in packaging and other applications. It is the second highest volume petrochemical feedstock after ethylene. Propylene and benzene are converted to acetone and phenol via the cumene process. Propylene is also used to produce isopropanol (propan-2-ol), acrylonitrile, propylene oxide (epoxypropane) and epichlorohydrin.

These chemicals are then used to make biobased durable products, for example, products in the electronic and automotive industries.

Starting with biomass containing poly-3-hydroxybutyrate (PHB), the monomer component obtained by heating the PHB biomass is primarily trans-crotonic acid. The crotonic acid is subsequently converted to produce acrylic acid, acrylic esters and butanol using multiple tandem metathesis catalysis reactions. Described herein are materials and processes needed to produce these various chemicals from biomass containing PHB.

Accordingly, methods of producing a crotonic acid in a PHA biomass, by reacting the crotonic acid under suitable conditions to form a lower alkyl crotonate ester, reacting the lower alkyl crotonate ester under suitable conditions to form a lower alkyl acrylate and a butene via cross-metathesis in the presence of a first catalyst with a sufficient amount of proplylene are described. The propylene is formed by a separate metathesis reaction of ethylene and 2-butene in the presence of a second catalyst while excess propylene is continuously removed. In certain embodiments, the methods further include reacting the crotonate ester under suitable conditions in the presence of a third catalyst to form an alcohol.

The invention also pertains to a method of producing a crotonic acid in a PHA biomass, reacting the crotonic acid under suitable conditions to form a butyl crotonate ester, and hydrogenating the butyl crotonate ester to form two moles of butanol.

In another aspect of the invention, a process for producing a lower alkyl acrylate is described. The process includes growing a genetically engineered PHA biomass to produce poly-3-hydroxybutyrate, pyrolyzing (heating at high temperature, or by torrefication) the poly-3 hydroxybutyrate to produce crotonic acid, reacting the crotonic acid under suitable conditions to form a lower alkyl crotonate ester, reacting the lower alkyl crotonate ester under suitable conditions to form a lower alkyl acrylate and a butene via cross metathesis in the presence of a first catalyst with a sufficient amount of propylene.

In yet another aspect of the invention a continuous biorefinery process for production of acrylic acid from PHA biomass using a multiple tandem catalysis reaction protocol is described. The process includes growing a genetically engineered PHA biomass to produce poly-3-hydroxybutyrate, pyrolyzing the poly-3 hydroxybutyrate to produce crotonic acid, reacting the crotonic acid under suitable conditions to form a lower alkyl crotonate ester in the presence of an esterification catalyst; reacting the lower alkyl crotonate ester under suitable conditions to form a lower alkyl acrylate and a butene via cross-metathesis in the presence of a first metathesis catalyst with a sufficient amount of propylene. The propylene is formed from a separate metathesis reaction of ethylene and 2-butene in the presence of a second metathesis catalyst and excess propylene is continuously removed. The product yields are optimized by separating out the reactions and selecting appropriate catalysts.

The method includes a multiple tandem catalytic reaction method that provides an efficient process for the high yield production of acrylic acid and acrylate ester products derived from crotonic acid. In certain embodiments, the residual biomass, after PHA conversion to crotonic acid, is utilized as an energy source.

A "metathesis catalyst" may be used alone or in combination with one or more additional catalysts. The metathesis reaction is conducted in the presence of a catalytically effective amount of a metathesis catalyst. The term "metathesis catalyst" includes any catalyst or catalyst system which catalyzes the metathesis reaction. The fundamental function of a metathesis catalyst is to facilitate the rearrangement of carbon-carbon double bonds through an activated metal coordination process. As such, these catalysts can be utilized to couple (cross metathesis or CM), cleave, ring-open (ROM), ring-close (RCM) or polymerize (ROMP) a range of olefinic compounds. Particularly useful metathesis catalysts are the Grubbs catalysts which are based on a central ruthenium atom surrounded by five ligands: two neutral electron-donating groups, two mono-anionic groups and one alkylidene group. The newest generation of ruthenium metathesis catalysts have the advantages of being able to be handled in air, react at relatively low temperatures and are tolerant to various olefinic functional groups including protic groups such as alcohols and acids all while maintaining high catalyst activity (S. Connon, S. Bleichert (2003), *Ang. Chem. Int. Ed.*, 42, p1900).

These synthetic catalysts represent a breakthrough technology which allows metathesis chemistry to be applied to functional molecules such as unsaturated vegetable oil derived fatty acids, fatty acid esters, hydroxyl fatty acids and unsaturated polyol esters. Exemplary metathesis catalysts include metal carbene catalysts based upon transition metals, for example, ruthenium, molybdenum, osmium, chromium, rhenium, and tungsten. Exemplary ruthenium-based metathesis catalysts Ruthenium-based metathesis catalysts, referred to generally as Grubb's catalysts are particularly useful in olefin methathesis. Metathesis catalysts include the original "first generation catalysts," "second-generation catalysts" (See Schrodi and Pederson, *Aldrichimica ACTA* Vol 40 (2) 45-52 (2007) and U.S. Pat. No. 7,329,758) and "Hovedyda-Grubbs analogs." These catalysts are especially useful in reactions with oxygenated compounds.

Many factors influence the complex catalytic pathways of olefin metathesis. Present metathesis catalytic technologies have limitations including catalytic deactivation, low catalytic turnover, catalytic instability and degradation and poor selectivity to name a few. These limitations result in low yield of product and increased costs.

Catalytic turnover is the number of moles of substrate that a mole of catalyst can convert before becoming inactivated. It has been estimated that for olefin metathesis to yield sufficient product in an economically viable biorefinery process, the catalytic turnover should be greater than fifty thousand. (Burdett et al., *Oganometallics* 23: 2027-2047 (2004)).

Deactivation of the metathesis catalyst often involves terminal olefin inhibition with accumulation of unsaturated products. Limiting deactivation of the metathesis catalyst when converting ethylene and butylenes to propylene is accomplished by pretreating or conditioning the catalyst with cis 2-butene, whereas pretreatment with ethylene correlated with catalytic deactivation. (See Lysenko et. al., *J. of Organometallic Chem.*, 691: 5197-5203 (2006)).

The multiple tandem catalytic reactions and process described herein allows for selectivity, reduced deactivation and other reaction conditions increasing the yield of acrylic acid product. Crotonic acid is a carboxylic acid with a double bond between carbons C2 and C3. Free carboxylic acids and ethylene deactivate metathesis catalysts. By converting crotonic acid to acrylic acid in a multiple tandem catalytic process, the metathesis catalysts are reaction specific and are not exposed to the free carboxylic acid or to ethylene. Each step of the overall reaction is separated out and optimized for high yield.

In the first stage of an exemplary process illustrating the multiple tandem catalytic process, crotonic acid is converted to the butyl crotonate ester using an esterification catalyst. In the second stage, ethylene and 2-butene are converted to propylene using a catalyst which is not sensitive to deactivation by ethylene. The selectivity of the reaction is maximized by continuous removal of the propylene which limits any unwanted side reactions. Finally in the third stage, the propylene is reacted with the butyl crotonate using another different specific metathesis catalyst to produce butyl acrylate and 2-butene.

Figure 12:
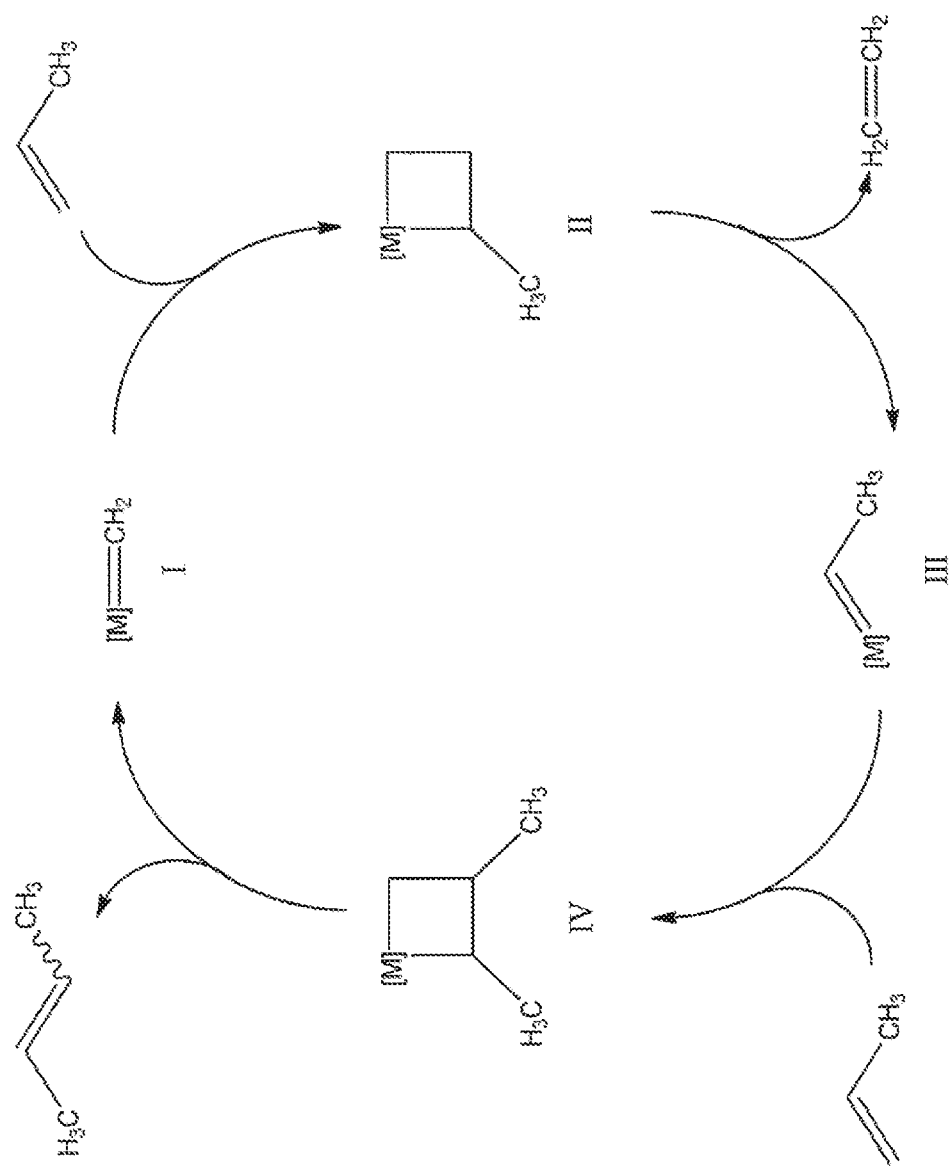
FIG. 12 is a schematic of the catalytic cycle for the self-metathesis of propylene to yield 2-butene and ethylene.

FIG. 12 details the general methathesis reaction of propylene to yield butane and ethylene. The starting point for the catalytic cycle is metal carbene (I). This reacts with propylene to generate the metallocyclobutane intermediate (II). This four-membered ring then fragments in the opposite direction to release ethylene and create a new metal carbene (III), which reacts with another equivalent of propylene. Fragmentation of the resulting metallocyclobutane (IV) produces 2-butene and regenerates the initial metal carbine (I) which then re-enters the catalytic cycle.

In certain embodiments of the invention, a metathesis catalyst is used in the reaction in the absence of ethylene or other deactivating product or side product. In other embodiments, a metathesis catalyst is insensitive to ethylene or other deactivating compounds. In other embodiments, the metathesis catalysis reacts with an asymmetrical alkene, e.g. propylene.

Selectivity and reaction rates of each stage of the process described herein can be optimized by the selection of the appropriate metathesis catalyst. Catalysts having a desirable activity under each step of the multiple tandem catalytic reaction under varying reaction conditions can be designed and tested by comparing the rate of product formation. New metathesis catalysts are being developed to meet the need for the industrial production of biochemicals where the catalysts are more active and perform more difficult transformations selectively in a variety of reactions conditions with unique reactivity and tailored initiation rates. These metathesis catalysts will be tailored to the stability, reactivity and selectivity needed for the metathesis reaction desired. Also contemplated herein, are developing new metathesis catalysts that improve the reactivity, selectivity or initiation rate of the methods described herein. Optimizing the metathesis catalyst for specific reactions is possible by changing the ligand groups attached to the metallic center. For example, it was found that depending on the type of detachable phosphine ligands utilized in Grubbs catalysts, the initiation rate of the metathesis reaction could be controlled. This is important when considering that depending on the application, it is advantageous to employ catalysts that initiate either more slowly (e.g. for ROMP reactions) or more quickly (e.g. low temperature reactions).

Commercial sources of metathesis catalysts include Sigma-Aldrich, Materia and Elevance (U.S. Patent Publication No. US 2009/0264672).

Additional exemplary metathesis catalysts include, without limitation, metal carbene complexes selected from the group consisting of molybdenum, osmium, chromium, rhenium, and tungsten. The term "complex" refers to a metal atom, such as a transition metal atom, with at least one ligand or complexing agent coordinated or bound thereto. Such a ligand typically is a Lewis base in metal carbene complexes useful for alkyne or alkene-metathesis. Typical examples of such ligands include phosphines, halides and stabilized carbenes. Some metathesis catalysts may employ plural metals or metal co-catalysts (e.g., a catalyst comprising a tungsten halide, a tetraalkyl tin compound, and an organoaluminum compound).

An immobilized catalyst can be used for the metathesis process. An immobilized catalyst is a system comprising a catalyst and a support, the catalyst associated with the support. Exemplary associations between the catalyst and the support may occur by way of chemical bonds or weak interactions (e.g. hydrogen bonds, donor acceptor interactions) between the catalyst, or any portions thereof, and the support or any portions thereof. Support is intended to include any material suitable to support the catalyst. Typically, immobilized catalysts are solid phase catalysts that act on liquid or gas phase reactants and products. Exemplary supports are polymers, silica or alumina. Such an immobilized catalyst may be used in a flow process. An immobilized catalyst can simplify purification of products and recovery of the catalyst so that recycling the catalyst may be more convenient.

The metathesis process can be conducted under any conditions adequate to produce the desired metathesis products. For example, stoichiometry, coordination chemistry between the catalyst and substrates, atmosphere, solvent, temperature and pressure can be selected to produce a desired product and to minimize undesirable byproducts. The metathesis process may be conducted under an inert atmosphere. Similarly, if the olefin reagent is supplied as a gas, an inert gaseous diluent can be used. The inert atmosphere or inert gaseous diluent typically is an inert gas, meaning that the gas does not interact with the metathesis catalyst to substantially impede catalysis. For example, particular inert gases are selected from the group consisting of helium, neon, argon, nitrogen and combinations thereof.

Similarly, if a solvent is used, the solvent chosen may be selected to be substantially inert with respect to the metathesis catalyst. For example, substantially inert solvents include, without limitation, aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc.

In certain embodiments, the metathesis reaction may also be accomplished without the use of solvents.

In other embodiments, a ligand may be added to the metathesis reaction mixture. In many embodiments using a ligand, the ligand is selected to be a molecule that stabilizes the catalyst, and may thus provide an increased turnover number for the catalyst. In some cases the ligand can alter reaction selectivity and product distribution. Examples of ligands that can be used include Lewis base ligands, such as, without limitation, trialkylphosphines, for example tricyclohexylphosphine and tributyl phosphine; triarylphosphines, such as triphenylphosphine; diarylalkylphosphines, such as, diphenylcyclohexylphosphine; pyridines, such as 2,6-dimethylpyridine, 2,4,6-trimethylpyridine; as well as other Lewis basic ligands, such as phosphine oxides and phosphinites. Additives may also be present during metathesis that increase catalyst lifetime.

Any useful amount of the selected metathesis catalyst can be used in the process. For example, the molar ratio of the reagent to catalyst may range from about 5:1 to about 10,000,000:1 or from about 50:1 to 500,000:1.

The metathesis reaction temperature may be a rate-controlling variable where the temperature is selected to provide a desired product at an acceptable rate. The metathesis temperature may be greater than −40° C., may be greater than about −20° C., and is typically greater than about 0° C. or greater than about 20° C. Typically, the metathesis reaction temperature is less than about 150° C., typically less than about 120° C. An exemplary temperature range for the metathesis reaction ranges from about 20° C. to about 120° C.

The metathesis reaction can be run under any desired pressure. Typically, it will be desirable to maintain a total pressure that is high enough to keep the cross metathesis reagent in solution. Therefore, as the molecular weight of the cross metathesis reagent increases, the lower pressure range typically decreases since the boiling point of the cross-metathesis reagent increases. The total pressure may be selected to be greater than about 10 kPa, in some embodiments greater than about 30 kPa, or greater than about 100 kPa. Typically, the reaction pressure is no more than about 7000 kPa, in some embodiments no more than about 3000 kPa. An exemplary pressure range for the metathesis reaction is from about 100 kPa to about 3000 kPa. Additionally pH can range from about 2-10.

In some embodiments, the metathesis reaction is catalyzed by a system containing both a transition and a non-transition metal component. The most active and largest number of metathesis catalyst systems are derived from Group VI A transition metals, for example, tungsten and molybdenum.

The use of the metathesis catalyst in olefin cross metathesis allows for product selectivity and olefin reactivity. (A. Chatterjee et al., J. Am. Chem. Soc. 125:11360-11370 (2003)).

Exemplary catalysts include but are not limited to the following:

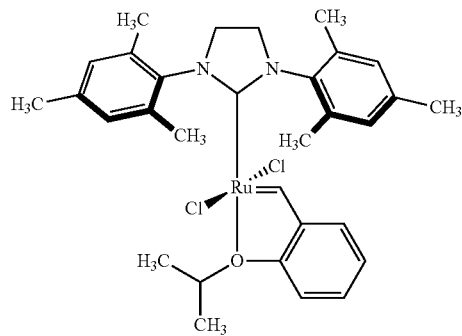

2nd Gen. Hoveyda-Grubbs Catalyst
(1,3-Bis-(2,4,6-trimethylphenyl)-2-imidazolidinylidene)dichloro(o-isopropoxyphenylmethylene)ruthenium -continued

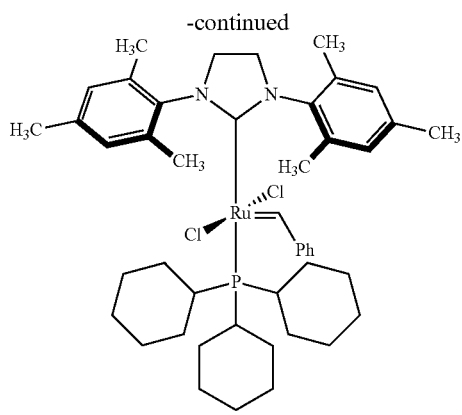

2nd Gen. Grubbs Catalyst
1,3-Bis-(2,4,6-trimethylphenyl)-2-
(imidazolidinylidene)(dichloro-
phenylmethylene)(tri-
cyclohexylphosphine)ruthenium

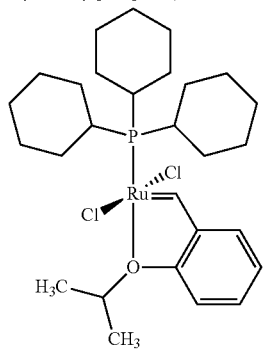

1st Gen. Hoveyda-Grubbs Catalyst
1,3-Bis-(2,4,6-trimethylphenyl)-2-
(imidazolidinylidene)(dichloro-
phenylmethylene)(tri-
cyclohexylphosphine)ruthenium

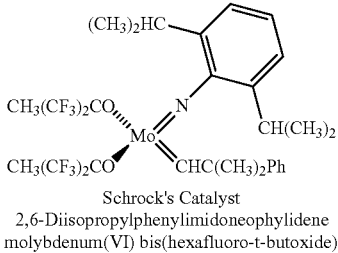

Schrock's Catalyst
2,6-Diisopropylphenylimidoneophylidene
molybdenum(VI) bis(hexafluoro-t-butoxide)

Continuous Biorefinery Process

Useful embodiments of the continuous biorefinery process are the production of biobased acrylic acids and related products derived by multiple tandem catalytic reactions from PHA biomass derived crotonic acid. This process is a highly efficient conversion of carbon from a biosource to acrylic acid and related products for use in a variety of applications.

Residual Biomass

As used herein, "pyrolysis liquids" are defined as a low viscosity fluid with up to 15-20% water, typically containing sugars, aldehydes, furans, ketones, alcohols, carboxylic acids and lignins Also known as bio-oil, this material is produced by pyrolysis, typically fast pyrolysis of biomass at a temperature that is sufficient to decompose at least a portion of the biomass into recoverable gases and liquids that may solidify on standing. In some embodiments, the temperature that is sufficient to decompose the biomass is a temperature between 400° C. to 800° C.

In other embodiments, the process includes torrefying the residual biomass. In certain embodiments, the torrefying includes maintaining the residual biomass at a temperature of 200° C. to 350° C. In other embodiments, the torrefying includes maintaining the residual biomass at a temperature for a time period of 10 to 30 minutes, for example, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes or greater than 30 minutes.

As used herein, "torrefying" refers to the process of torrefication, which is an art-recognized term that refers to the drying of biomass. The process typically involves heating a biomass in a range from 200-350° C., over a relatively long duration (e.g., 10-30 minutes), typically in the absence of oxygen. The process results in a torrefied biomass having a water content that is less than 7 wt % of the biomass. The torrefied biomass may then be processed further.

Applications

The biobased chemicals produced from the biomass (e.g., crotonic acid, acrylic acid, propylene, butane etc.) can be utilized a starting materials for a wide variety of applications. For example, acrylic acid and its esters readily combine with themselves or other monomers (e.g. acrylamides, acrylonitrile, vinyl, styrene, and butadiene) by reacting at their double bond, forming homopolymers or copolymers which are used in the manufacture of various plastics, paper manufacture and coating, exterior house paints for wood and masonry, coatings for compressed board and related building materials, flocculation of mineral ore fines and waste water, and treatment of sewage, printing inks, interior wall paints, floor polishes, floor and wall coverings, industrial primers, textile sizing, treatment and finishing, leather impregnation and finishing and masonry sealers, coatings, adhesives, elastomers, as well as floor polishes, and paints. Acrylic acid is also used in the production of polymeric materials such polyacrylic acid, which is a major component of superabsorbant diapers.

Likewise, propylene is raw material for a wide variety of products including polypropylene, a versatile polymer used in packaging and other applications. It is the second highest volume petrochemical feedstock after ethylene. Propylene and benzene are converted to acetone and phenol via the cumene process. Propylene is also used to produce isopropanol (propan-2-ol), acrylonitrile, propylene oxide (epoxypropane) and epichlorohydrin.

EXAMPLES

The present technology is further illustrated by the following examples, which should not be construed as limiting in any way.

Experimental Methods

Measurement of Thermal Degradation Products by Pyrolysis-Gas Chromatography-Mass Spectroscopy (Py-GC-MS)

In order to identify and semi-quantitate the monomer compounds generated from dry biomass while being heated at various temperatures, an Agilent 7890A/5975 GC-MS equipped with a Frontier Lab PY-2020iD pyrolyzer was used. For this technique, a sample is weighed into a steel cup and loaded into the pyrolyzer autosampler. When the pyrolyzer and GC-MS are started, the steel cup is automatically placed into the pyrolyzer which has been set to a specific temperature. The sample is held in the pyrolyzer for a short period of time while volatiles are released by the sample. The volatiles are then swept using helium gas into the GC column where they condense onto the column which is at room temperature. Once the pyrolysis is over, the GC column is heated at a certain rate in order to elute the volatiles released from the sample. The volatile compounds are then swept using helium gas into an electro ionization/mass spectral detector (mass range 10-700 daltons) for identification and quantitation.

For the following examples, 200-400 µg of dry biomass was weighed into a steel pyrolyzer cup using a microbalance. The cup was then loaded into the pyrolyzer autosampler. The pyrolyzer was programmed to heat to a temperature of 300-350° C. for a duration of 0.2-1 minutes. The GC column used in the examples was either a Frontier Lab Ultra Alloy capillary column or an HP-5MS column (length 30m, ID 0.25 µm, film thickness 0.25 µm). The GC was then programmed to heat from room temperature to 70° C. over 5 minutes, then to 240° C. at 10° C./min for 4 min. and finally to 270° C. at 20° C./min for 1.5 min. Total GC run time was 25 minutes. Peaks shown in the chromatograms were identified by the best probability match to spectra from a NIST mass spectral library.

Example 1

Figure 2:
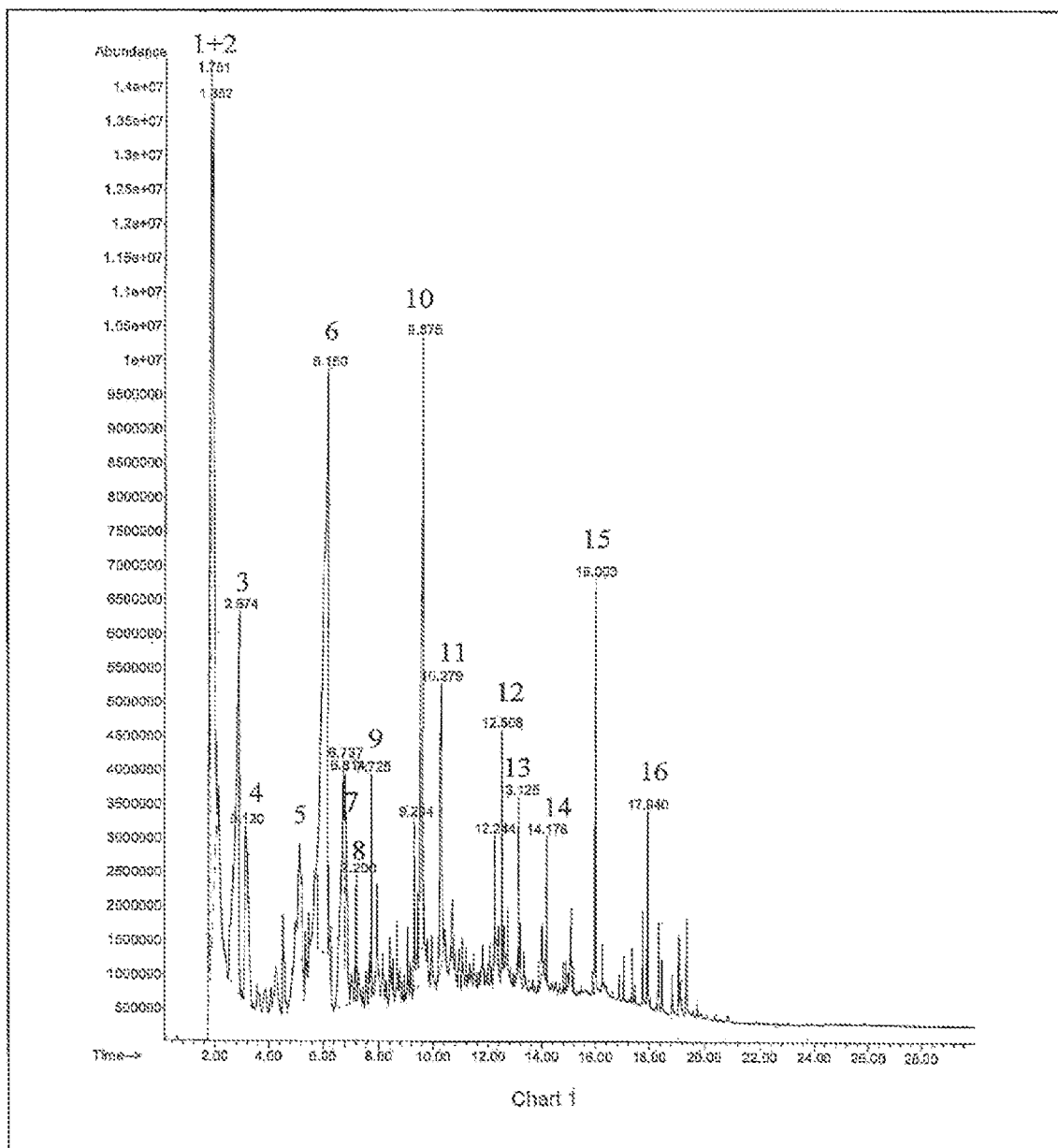
FIG. 2 is a gas chromatogram of tobacco+P3HB (10% by wt) pyrolyzed at 350° C., according to one embodiment.
Figure 3:
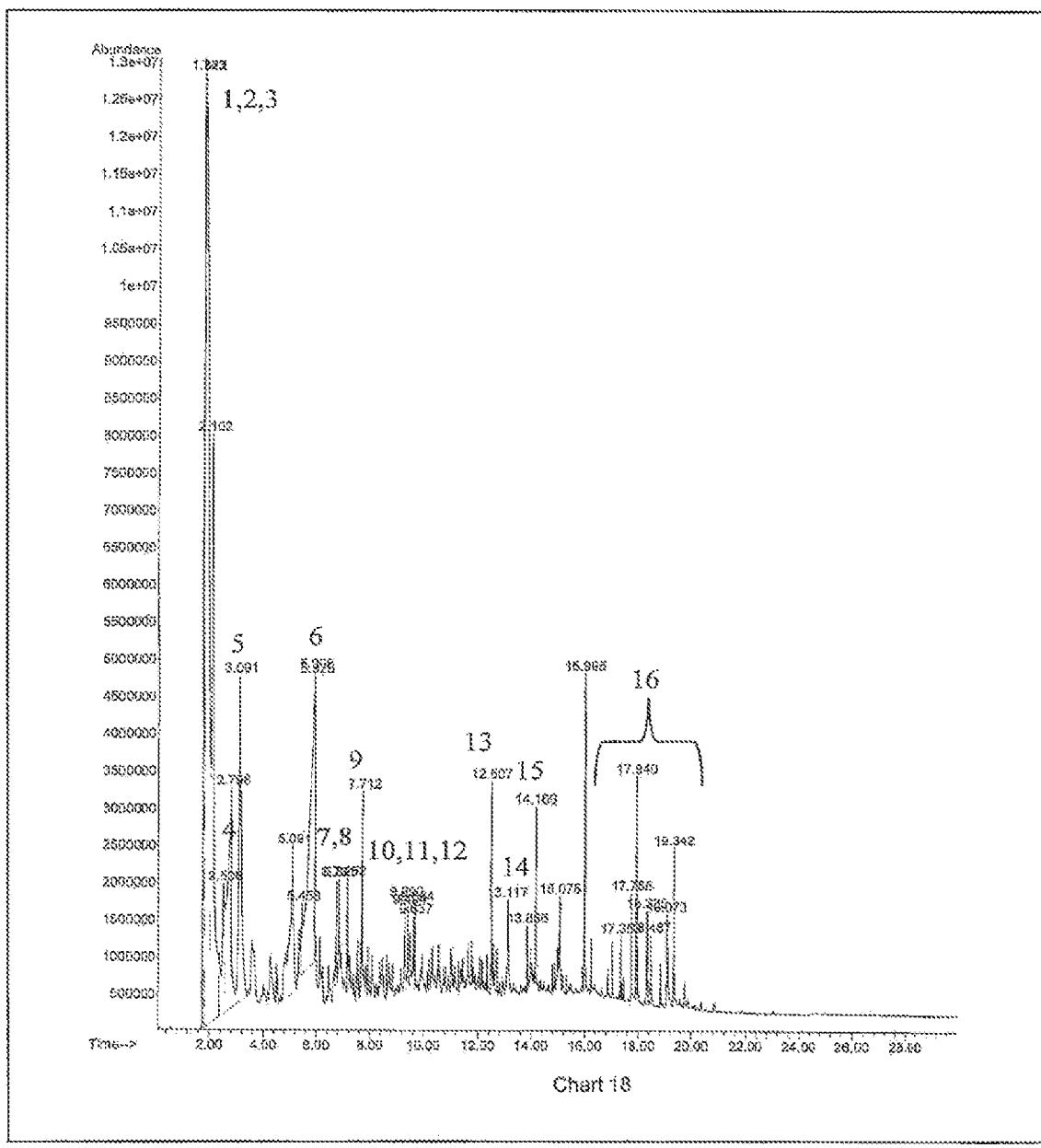
FIG. 3 is a gas chromatogram of tobacco+P3HB (10% by wt)+lime (5% by wt) pyrolyzed at 350° C., according to one embodiment.

Generation of Biobased Crotonic Acid from Pyrolysis of Genetically Engineered Tobacco Expressing Poly-3-hydroxybutyrate In this example, it is shown that heating of genetically engineered plant biomass containing poly-3HB generates biobased crotonic acid monomer. Tobacco was genetically engineered to express poly-3HB and cultivated under greenhouse conditions yielding plant biomass containing 10% poly-3HB on a dry leaf basis. Tobacco leaves were removed from their plants, dried to <5% by wt. moisture and manually milled to a particle size of <1 mm A portion of the tobacco leaf powder was then mixed with a aqueous lime slurry (Ca(OH)$_2$ 95%+Sigma Aldrich) and dried at 110° C. in an oven prior to being subject to Py-GC-MS at 350° C. The final concentration of lime in the dry tobacco biomass was 5% by weight. FIGS. 2 and 3 show the Py-GC-MS plots for the Tobacco without lime and with lime catalyst while Tables 1 and 2 list the chromatogram peak retention times and mass spectral library matches. The results show that at 350° C., the major compounds generated by heating the Tobacco with 10% poly-3HB were CO$_2$, acetic acid and crotonic acid. The first two volatile compounds originated from polysaccharides and hemicelluloses present in the Tobacco plant while the crotonic acid (cis and trans) originated from the poly-3HB. When lime was added to the Tobacco+poly-(3HB), the overall effect was to increase the relative amount of CO$_2$ generated. Addition of metal ions (potassium, calcium and lithium) to wood has been shown to increase the rates of certain pyrolysis reactions especially decarboxylation reactions of lignin, hemicellulose and cellulose (G. Richards and G. Zheng, *J. of Anal. and Applied Pyrolysis*, 21 (1991), p133). This could account for the large increase in CO$_2$ generated during pyrolysis of the Tobacco after addition of the lime catalyst. The catalyst also appeared to suppress the generation of peaks with retention times in the 9-10 min. region which were identified as ester and alcohol-type compounds.

TABLE 2

GC-MS peak retention times and compounds generated during pyrolysis @350° C. of Tobacco with 10% poly-3HB.

| Peak # | Retention Time (min) | Peak ID |
|---|---|---|
| 1 | 1.781 | CO$_2$ |
| 2 | 1.852 | CO$_2$ |
| 3 | 2.874 | Acetic acid |
| 4 | 3.120 | 1-Hydroxy-2-propanone |
| 5 | 5.132 | Cis-crotonic acid |
| 6 | 6.150 | Trans-crotonic acid |
| 7 | 6.810 | 2-Methyl-1,3-butanediol |
| 8 | 7.200 | 2-Hydroxy-3-methyl-2-cyclopentene-1-one |
| 9 | 7.725 | Cyclopropylmethanol |
| 10 | 9.575 | Cyclopropanecarboxylic acid ethyl ester |
| 11 | 10.279 | 3-Ethyl-3-pentanol |
| 12 | 12.508 | 2,6,10-Trimethyl-14-ethylene-14-pentadecene |
| 13 | 13.125 | Hexadecanoic acid |
| 14 | 14.178 | Methano-azulene compound |
| 15 | 16.003 | 1-Acetyl-2-pyridinyl-2,3,4,5-tetra-hydropyrrole |
| 16 | 17.940 | Octacosane |

TABLE 3

GC-MS peak retention times and compounds generated during pyrolysis @350° C. of Tobacco with 10% poly-3HB + 5% lime.

| Peak # | Retention Time (min) | Peak ID |
|---|---|---|
| 1 | 1.779 | CO$_2$ |
| 2 | 1.822 | CO$_2$ |
| 3 | 2.102 | CO$_2$ |
| 4 | 2.505-2.798 | Acetic acid |
| 5 | 3.091 | 1-Hydroxy-2-propanone |
| 6 | 5.839 | Trans-crotonic acid |
| 7 | 6.792 | 1-Vinyl pyrazole |
| 8 | 7.150 | 2-Hydroxy-3-methyl-2-cyclopentene-1-one |
| 9 | 7.712 | Cyclopropylmethanol |
| 10 | 9.287 | Indole |
| 11 | 9.400 | 2-Methoxy-4-vinylphenol |
| 12 | 9.637 | 2,6-dimethoxyphenol |
| 13 | 12.507 | 2,6,10-Trimethyl-14-ethylene-14-pentadecene |
| 14 | 13.117 | Hexadecanoic acid |
| 15 | 14.169 | Hexadecanamide |
| 16 | 17.353-19.074 | Eicosane, Tricontane, Octacosane |

Example 2

Lignocellulosic Hydrolysis Followed by Generation of Biobased Crotonic Acid from Pyrolysis of Genetically Engineered Tobacco Expressing Poly-3-hydroxybutyrate In this example, a process is described where plant biomass containing poly-3HB is first processed to remove soluble sugars and other components and then heated to generate biobased crotonic acid. Tobacco engineered to express poly-3HB at 10% by wt. in the leaf plant was harvested after growing to full size in a greenhouse. A total of 100 g of dried tobacco leaves containing about 10 g of PHA was collected and milled to <1 mm size. The milled leaves were then subjected to a standard hydrolysis procedure using dilute acid and enzyme yielding soluble sugars (40 g), unidentified solubles (20 g), and residual dried biomass (40 g). The residual biomass was analyzed by GC (see Doi, *Microbial Polyesters*, John Wiley& Sons, 1990, p24) indicating a total PHA content of about 8 g (80% recovery of PHA). This dried residue was subjected to pyrolysis GC at 350° C. yielding crotonic acid at recovery of 90% and purity of >95% (cis and trans combined).

Example 3

Generation of Biobased Acrylic Acid Ester from the Pyrolysis of a Genetically Engineered Biomass Producing Poly-3-hydroxybutyrate Followed by Crotonic Acid Metathesis In the previous example, it was shown how biomass+ poly-3HB could be used to generate biobased crotonic acid by heating to temperatures where thermal decomposition of poly-3HB is initiated. Crotonic acid recovered from this process could be further transformed into valuable chemical intermediates by using cross metathesis reactions. This example details a method for converting crotonic acid to acrylic acid esters using a multiple tandem catalyst process.

Cross metathesis is the coupling of two reactants containing unsaturated carbon bonds and has been historically limited to starting compounds that do not have any functional groups such as simple olefins (ethylene, propylene etc.). The ruthenium-based organic catalysts which are now being manufactured by Materia (U.S. Pat. Nos. 6,620,955 and 7,026,495) and developed by Elevance (U.S. Patent Application 2009/0264672) represent a breakthrough technology which allows cross metathesis chemistry to be applied to functional molecules such as unsaturated vegetable oil derived fatty acids, fatty acid esters, hydroxyl fatty acids and unsaturated polyol esters. Crotonic acid is another molecule (an unsaturated short chain carboxylic acid) that lends itself to this new form of cross metathesis with olefins such as ethylene, including bio-derived ethylene from ethanol dehydration, to produce acrylic acid esters. One challenge, however, in reacting ethylene monomer with metathesis catalysts is the propensity for the ethylene to deactivate or degrade the catalyst which leads to low rates of conversion and yield loss (Z. Lysenko et. al. (2006), *J. of Organometallic Chem.*, 691, p5197; X. Lin et. al. (2010), *J. of Molecular Catalysis A: Chemical*, 330, p99; K. Burdett et al. (2004), *Organometallics*, 23, p2027, incorporated by reference herein). This is especially important when developing industrial applications using metathesis catalysts for biobased chemical production.

Using a multiple tandem catalysis process where the primary metathesis catalyst (catalyst #3 below) is not exposed to ethylene is described herein. In the first stage of the process, crotonic acid is converted to the butyl crotonate ester using an esterification catalyst known to those skilled in the art but could include acids, alkaline metal hydroxides, alkoxides and carbonates, enzymes and non-ionic bases, such as amines, amidines, guanidines and triamino(imino) phosphoranes. The esterification reaction can also proceed via conversion of the crotonic acid to crotonyl chloride and then reacted with an alcohol. One advantage of the latter reaction is that it is not reversible. In the second stage, ethylene and 2-butene are converted to propylene using a catalyst which is not sensitive to deactivation by ethylene such as Schrock's molybdenum-alkylidene or tungsten-alkylidene catalysts (Schrock et al. (1988), *J. Am. Chem. Soc.*, 110, p1423). The selectivity of the reaction is maximized by continuous removal of the propylene which limits any unwanted side reactions. Finally in the third stage, the propylene is reacted with the butyl crotonate using a second generation Hoveyda-Grubb's catalyst (such as (1,3-bis(2,4, 6-trimethylphenyl)-2-imidazolidinylidene)dichloro(o-iso-propoxyphenylmethylene) ruthenium) to produce butyl acrylate and 2-butene. Catalysts of this type are used for reacting highly electron-deficient substrates at atmospheric pressure and temperatures of 5-30° C. In this reaction scheme, the metathesis catalyst is never exposed to ethylene and is therefore able to maintain the high reaction rates and high yields needed for industrial biochemical processes. The multiple tandem catalysis reactions for transforming crotonic acid to butyl acrylate are shown below:

Stage #1:

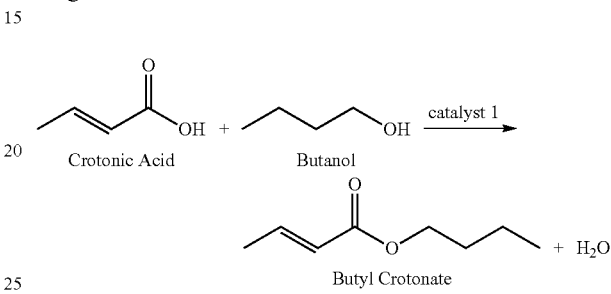

Stage #2:

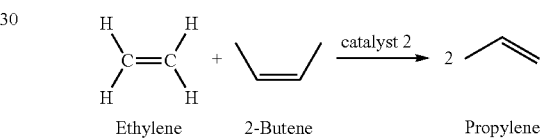

Stage #3:

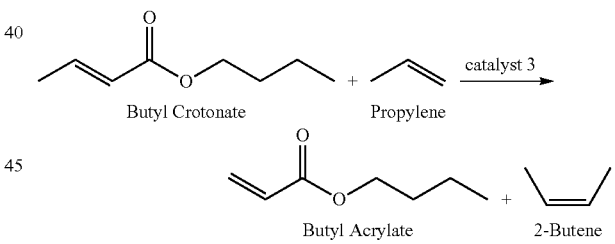

Key to the above transformation is the conversion of the crotonic acid to the ester (metathesis catalysts can be inactivated by free carboxylic acids) and the use of propylene and not ethylene for the conversion of the butyl crotonate to butyl acrylate. The use of other alcohols, like ethanol, would produce other acrylic acid esters.

The 2-butene produced via the Stage (3) reaction can be used as a chemical feedstock for conversion to butadiene or via metathesis with ethylene to propylene per Stage (2) reaction. In the case where ethylene is derived from renewably produced ethylene, the resulting propylene would be a completely biobased chemical product.

To carry out the above reactions on a lab scale, one could take 5 g microbial or plant biomass containing poly-3HB such as that described in Example 1 and heat at atmospheric pressure under nitrogen at 300° C. The vapors are then cooled with direct solidification of crotonic acid onto a cold surface held at 20° C. (crotonic melting point is 70° C.).

Figure 4:
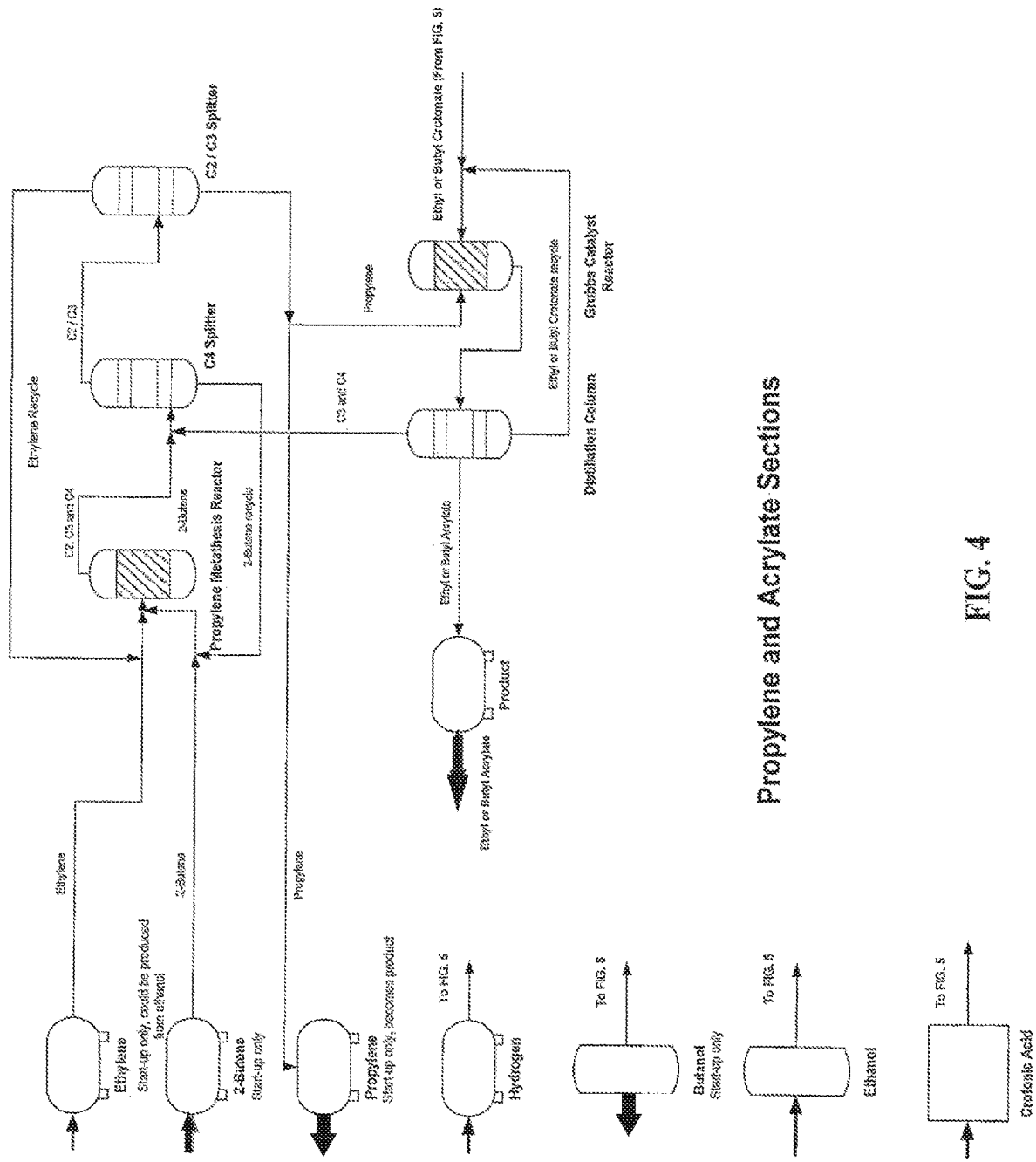
FIG. 4 is a process flow diagram for the production of biobased acrylic acid from biomass+P3HB using metathesis catalysts, according to one embodiment.
Figure 5:
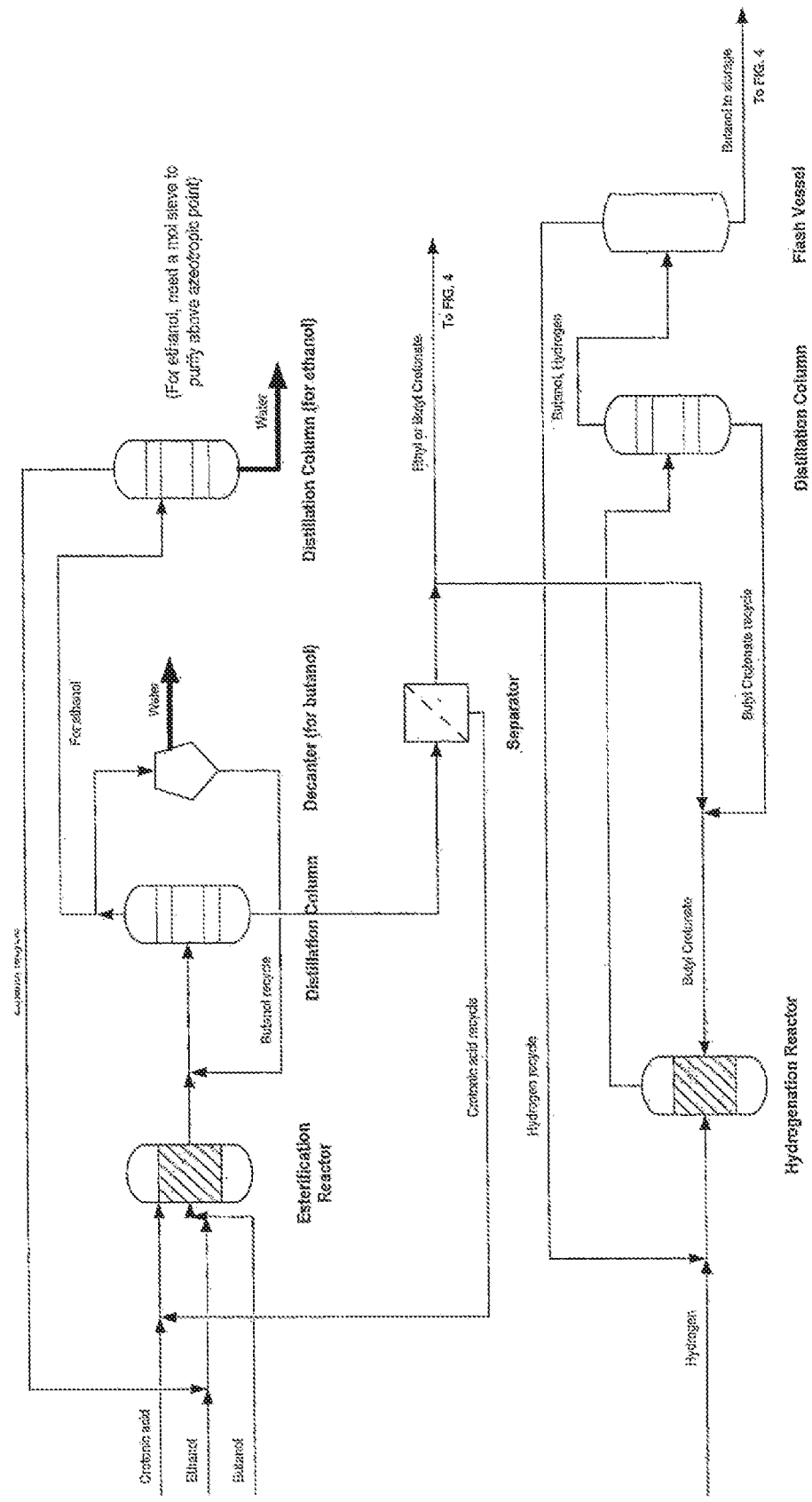
FIG. 5 is a process flow diagram for the esterification and hydrogenation of crotonic acid, according to one embodiment.

Approximately 3 g of crotonic acid is recovered for subsequent multiple tandem catalysis as outlined in the above reactions. FIG. 4 shows a Process Flow Diagram (PFD) illustrating the integrated industrial production of acrylate and propylene from crotonic acid and ethylene starting materials while FIG. 5 shows the esterification and hydrogenation of crotonic acid.

Example 4

Generation of Biobased Butanol from the Pyrolysis of a Genetically Engineered Biomass Producing Poly-3-hydroxybutyrate Followed by Crotonic Acid Direct Hydrogenation The following example describes the generation of biobased crotonic acid from biomass containing poly-3HB and then conversion of the crotonic acid to biobased butanol via hydrogenation. 5 g of microbial or plant biomass containing poly-3HB is heated at atmospheric pressure under nitrogen to 300° C. The generated vapors are cooled with direct solidification of crotonic acid onto a cold surface held at 20° C. (crotonic melting point is 70° C.). Approximately 3 g of crotonic acid is recovered for subsequent hydrogenation. A 50 mL autoclave is charged with 5 g of water, 2 g of crotonic acid and 0.3 g of a Ru—Sn—Pt catalyst as disclosed in Example 3 of U.S. Pat. No. 6,495,730. After flushing the autoclave with nitrogen, hydrogen gas is introduced followed by pressurizing the autoclave to 20 bar and elevating temperature to 180° C. After achieving target temperature the reactor is further pressurized to 150 bar and the hydrogenation reaction is allowed to proceed for 6 hours. Upon completion of the reaction, the reactor is cooled and de-pressurized followed by flushing with nitrogen. The autoclave contents are discharged and the catalyst separated by decantation. The catalyst is washed with additional DI water that is combined with the supernatant. An aliquot of supernatant is filtered and analyzed by HPLC to determined % conversion of crotonic acid and the % yield of butanol on a molar basis. Alternatively, the feed material for the above hydrogenation could be a crotonate ester like the butyl crotonate formed in Example 3. The butyl crotonate would then form 2 moles of butanol after hydrogenation. The reaction is shown below:
Hydrogenation Reaction:

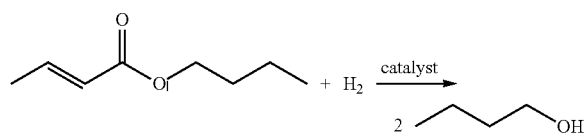

FIG. 5 shows the integrated industrial process for butanol production via hydrogenation and esterification of crotonic acid.

Example 5

Figure 6:
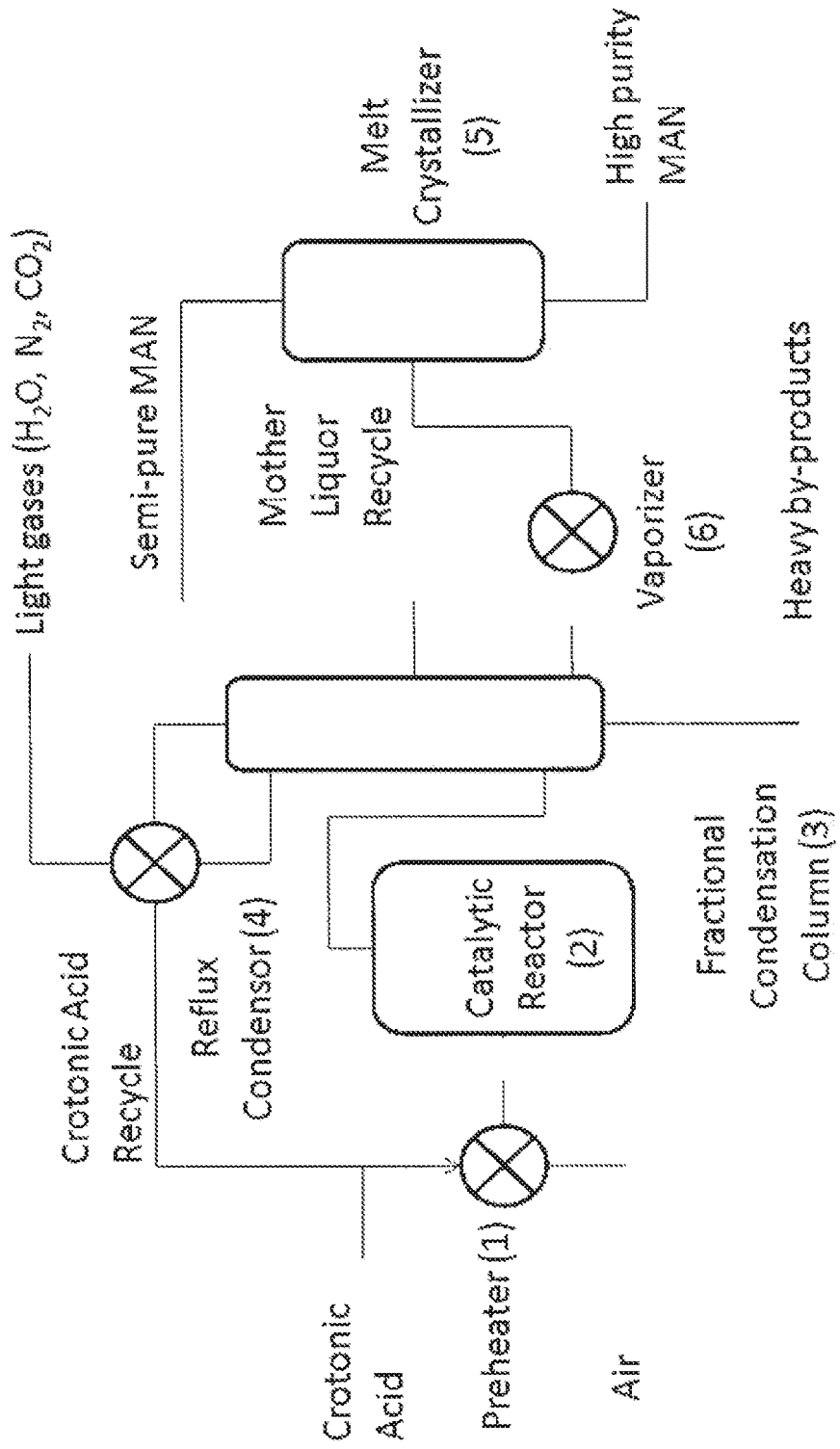
FIG. 6 is a process flow diagram for the oxidation of crotonic acid to maleic anhydride (MAN), according to one embodiment.

Generation of Biobased Maleic Anhydride By Pyrolysis of a Genetically Engineered Biomass Producing Poly-3-hydroxybutyrate Followed by Catalytic Oxidation This example shows how biobased maleic anhdyride (MAN) can be generated from biobased crotonic acid by catalytic oxidation. 5 g of microbial or plant biomass containing poly-3HB is subjected to heating at atmospheric pressure under nitrogen at 300° C. The generated vapors are cooled with direct solidification of crotonic acid onto a cold surface held at 20° C. (crotonic melting point is 70° C.). Approximately 3 g of crotonic acid is recovered for subsequent oxidation. The crotonic acid is fed with a pump through a liquid rotameter to the top of an electrically heated vaporizer where it is contacted with air fed through a separate rotameter to the bottom of the vaporizer. The vaporizer is operated at 150° C. to 200° C. and filled with stainless steel wool to ensure good heat transfer and efficient vaporization and mixing of crotonic acid and air. The mixture is then sent to an electrically heated preheater, also filled with stainless steel wool, and heated to 250° C. to 300° C. The vapor stream is sent to a fixed catalyst bed consisting of ⅛ alumina granules impregnated with vanadium pentoxide (as described in more detail in Church, J. M. and Bitha, P., "Catalytic air oxidation of crotonaldehyde to maleic anhydride", *I&EC Product Research and Development*, Vol. 2 (1), 1963, pp 61-66) contained within a jacketed reactor vessel. The reactor is heated electrically for start-up and cooled using circulating heat transfer oil to maintain reactor conditions. The exit gases are fed to a water cooled cyclone separator to allow the maleic anhydride and crotonic acid to condense. Any uncondensed product and still present in the light gases are then absorbed in a packed tower with circulating cold water used as direct contact scrubbing liquid. At the end of the run the liquid product from the cyclone separator and scrubbing liquid are collected and analyzed to calculate MAN yield (as percentage of theoretical) and conversion of crotonic acid. FIG. 6 shows a schematic diagram of the process for conversion of crotonic acid to maleic anhydride in more detail.

Example 6

Generation of δ-Valerolactone from a Genetically Engineered Microbe Producing Poly-5HV Microbial biomass containing poly-(5-valerolactone) (poly-5HV) was prepared by a fermentation process using procedures described in WO 2010/068953. A genetically modified *E. coli* strain specifically designed for production of poly-5HV from glucose syrup as a carbon feed source. After the fermentation was complete, 100 g of the fermentation broth (e.g. P5HV biomass) was mixed with an aqueous slurry containing 10% by weight lime ($Ca(OH)_2$ 95+%, Sigma Aldrich). A 2 g portion of the broth+P5HV+lime mixture was then dried in an aluminum weigh pan at 150° C. using an infrared heat balance (MB-45 Ohaus Moisture Analyzer) to constant weight. Residual water remaining was <5% by weight. The final lime concentration in the dry broth was 50 g lime/kg of dry solids or 5% by wt. A sample containing only dried fermentation broth+P5HV (no lime addition) was prepared as well. The samples were then analyzed by Py-GC-MS at a pyrolysis temperature of 300° C.

Figure 7:
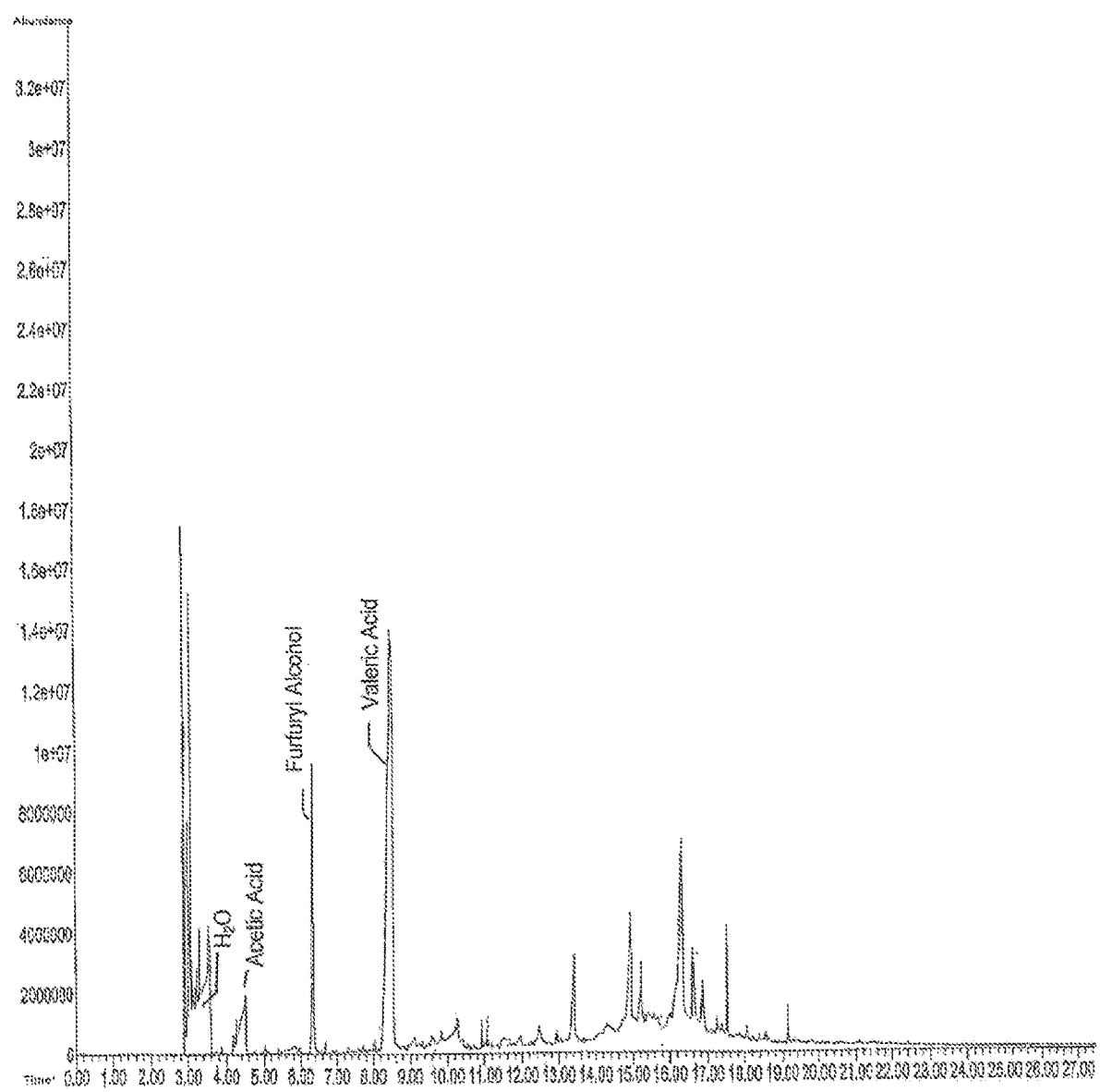
FIG. 7 is a gas chromatogram of dry microbial biomass+P5HV pyrolyzed at 300° C., according to one embodiment.
Figure 8:
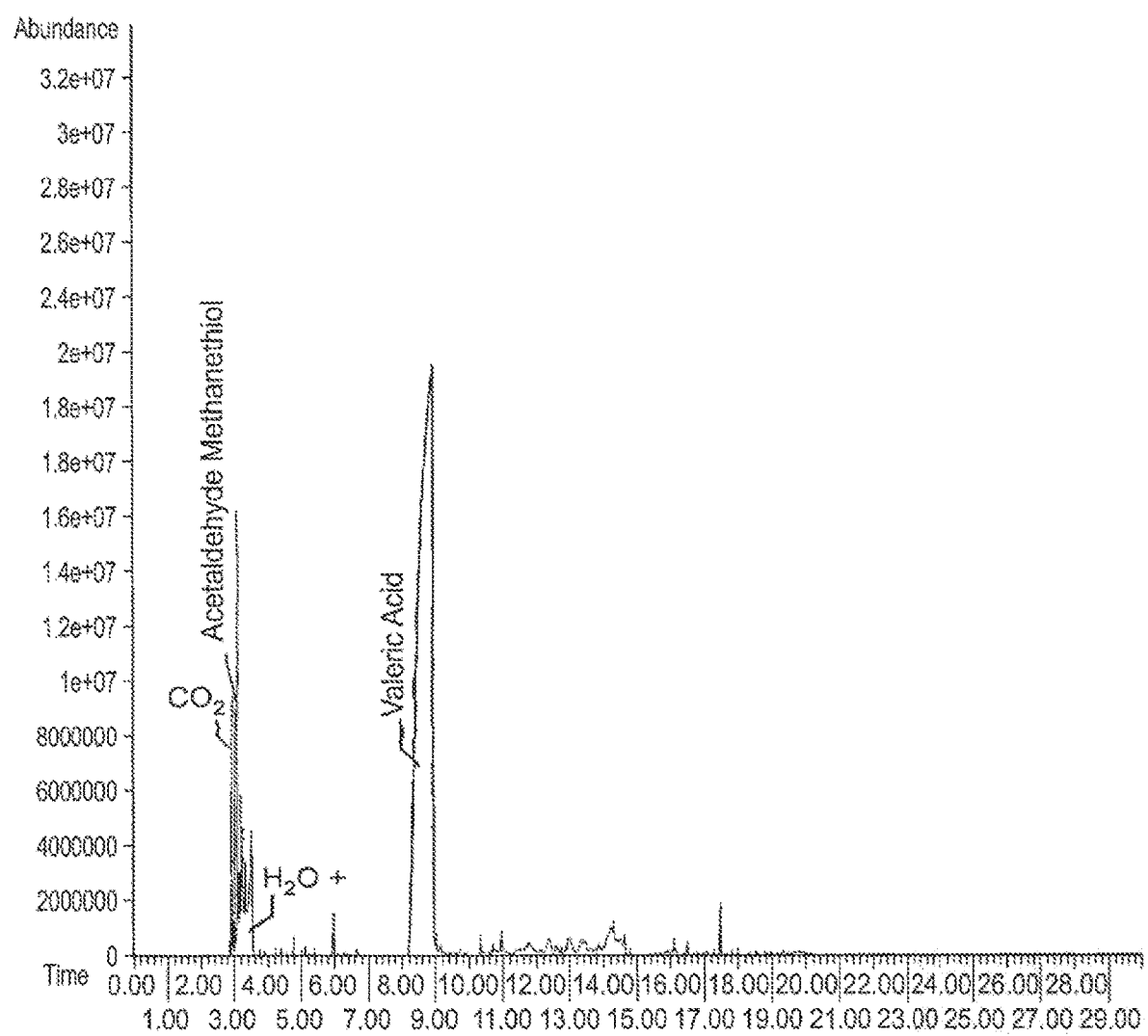
FIG. 8 is a gas chromatogram of dry microbial biomass+P5HV+lime (5% by wt.) pyrolyzed at 300° C., according to one embodiment.

FIGS. 7 and 8 show the GC-MA chromatograms for dried broth+poly-5HV and dried broth+poly-5HV with 5% lime added respectively. In the chromatograms, the compounds corresponding to the major GC peaks are also listed. Minor compounds generated at 300° C. from the samples included $CO_2$, acetic acid, acetaldehyde and water seen at the beginning of the GC chromatogram. The major compounds generated from heating the samples to 300° C. were valerolactone (labeled as valeric acid) at retention time 8.7 minute and an impurity at 6.3 minutes identified as furfuryl alcohol. The poly-5HV was the source for the valerolactone compound and likely unmetabolized sugar was the source of the furfuryl alcohol. The addition of the lime catalyst to the biomass+poly-5HV was shown to inhibit the generation of furfuryl alcohol and also a group of unidentified peaks at 14-18 minutes. The generation of furfuryl alcohol was also shown to be dependent on the temperature used for the reactive pyrolysis. For example, when the heating was carried out at 250° C., the generation of furfuryl alcohol from dry broth+poly-5HV was much less than at 300° C.

Example 7

Generation of Biobased Acrylic Acid from the Pyrolysis of Plant-Derived Poly-3-hydroxypropionate In this example, the feasibility of generating acrylic acid by pyrolysis of a plant biomass source of poly-3-hydroxypropionate (poly 3-HP) is shown.

Poly-3HP was prepared by fermentation using a genetically modified *E. coli* strain specifically designed for production of poly-3HP from glucose syrup as a carbon feed source. Examples of the *E. coli* strains, fermentation conditions, media and feed conditions are described in U.S. Pat. Nos. 6,316,262; 6,323,010; 6,689,589; 7,081,357; 7,202,064 and 7,229,804. The poly-3HP was solvent extracted from the microbial biomass using methyl propyl ketone heated to 75° C. Cold heptane was then added to the solution to precipitate poly-3HP. The precipitate was then filtered, washed with methanol and vacuum dried overnight. Wild-type switch grass, as described in U.S. Patent Publication No. US 2009/0271889 A1 was grown under greenhouse conditions and the senescent leaves collected after turning brown and drying on the plant. The leaves were then mixed with 10% by weight aqueous solutions containing either sodium carbonate ($Na_2CO_3$, 99.5+%, Sigma Aldrich) or hydrated ferrous sulfate ($FeSO_4$ $7H_2O$, JT Baker, 222 Red School Lane, Phillipsburg, N.J. 08865). Various catalysts available for conversion of 3HP to acrylic acid are described in U.S. Pat. No. 2,361,036. After mixing, the switch grass+catalyst mixtures were then dried at 110° C. and cryoground using a Spex Sample Prep 6870 Freezer Mill. Final particle size was <0.5 mm.

Dried samples of switch grass+catalyst+poly-3HP were analyzed by Py-GC-MS in order to identify the compounds produced during pyrolysis of poly-3HP in the presence of plant biomass at 300° C. To prepare the pyrolysis samples, the poly-3HP was first dissolved in chloroform to 5% by weight and added dropwise to a steel pyrolysis autosampler cup. The switch grass+catalyst dry mixture was then added to the cup and the chloroform evaporated off under vacuum. The weight percent poly-3HP in the dried biomasses mixture was targeted to 20% while the catalyst was targeted to 5% by weight dry biomass. Pyrolysis sample cups containing only switch grass and poly-3HP at 20% by weight were also prepared and analyzed for comparative purposes.

Figure 9:
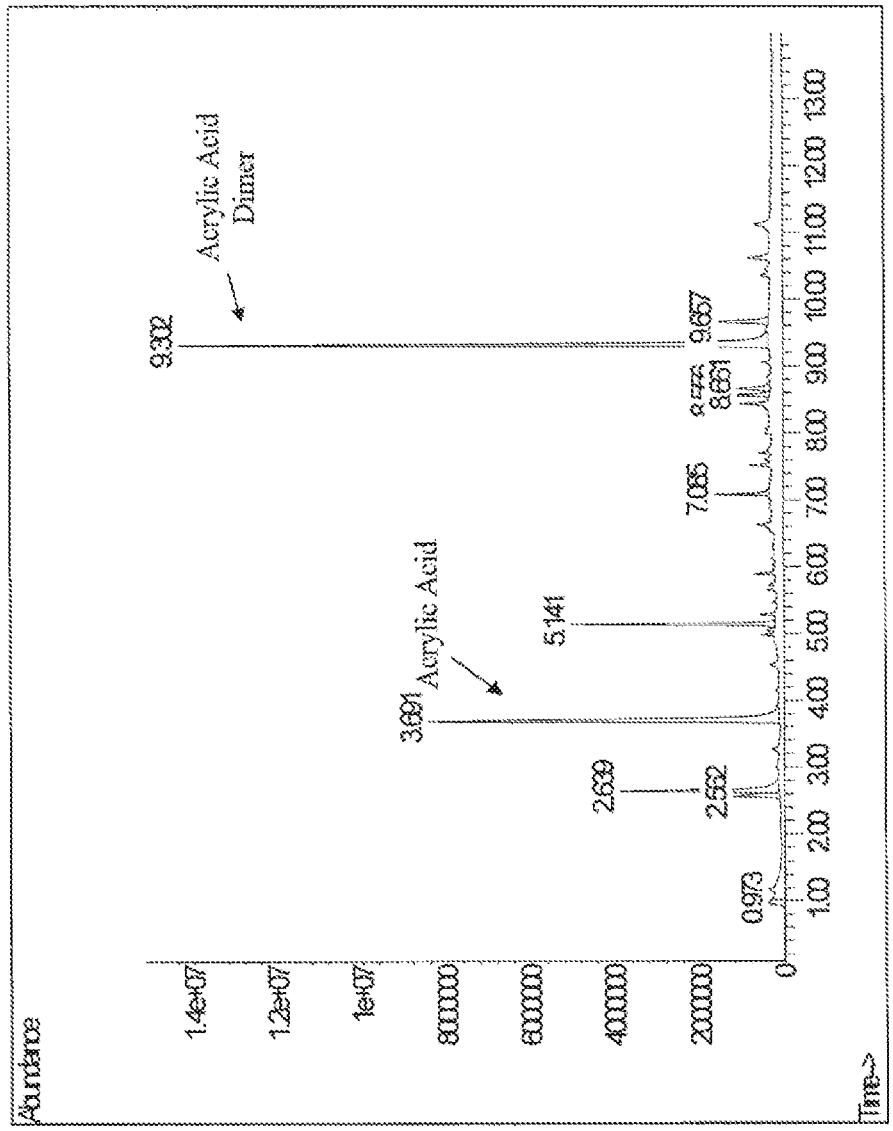
FIG. 9 is a gas chromatogram of dry switch grass+P3HP pyrolyzed at 300° C., according to one embodiment.
Figure 10:
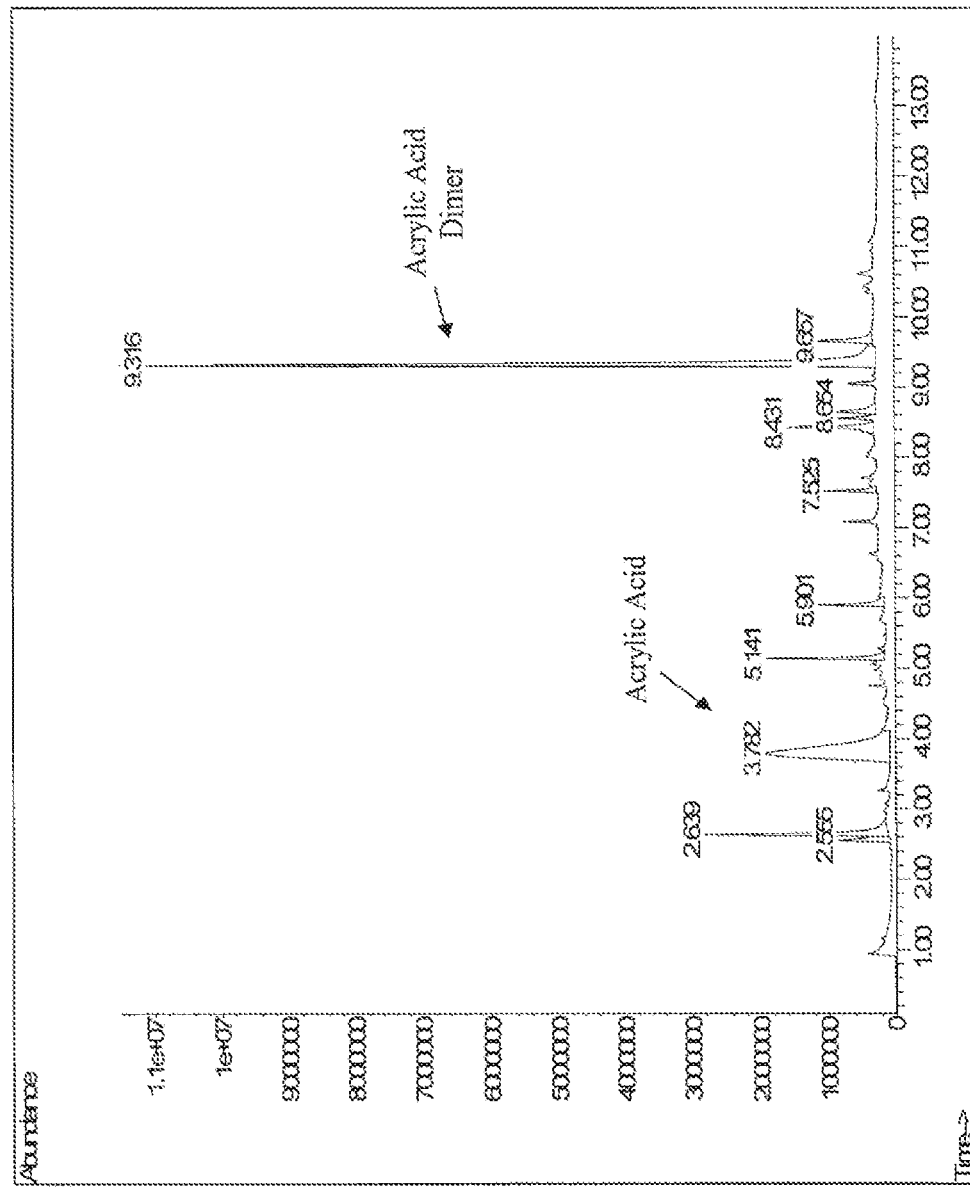
FIG. 10 is a gas chromatogram of dry switch grass+P3HP+$FeSO_4$ 7 $H_2O$ (5% wt.) pyrolyzed at 300° C., according to one embodiment.
Figure 11:
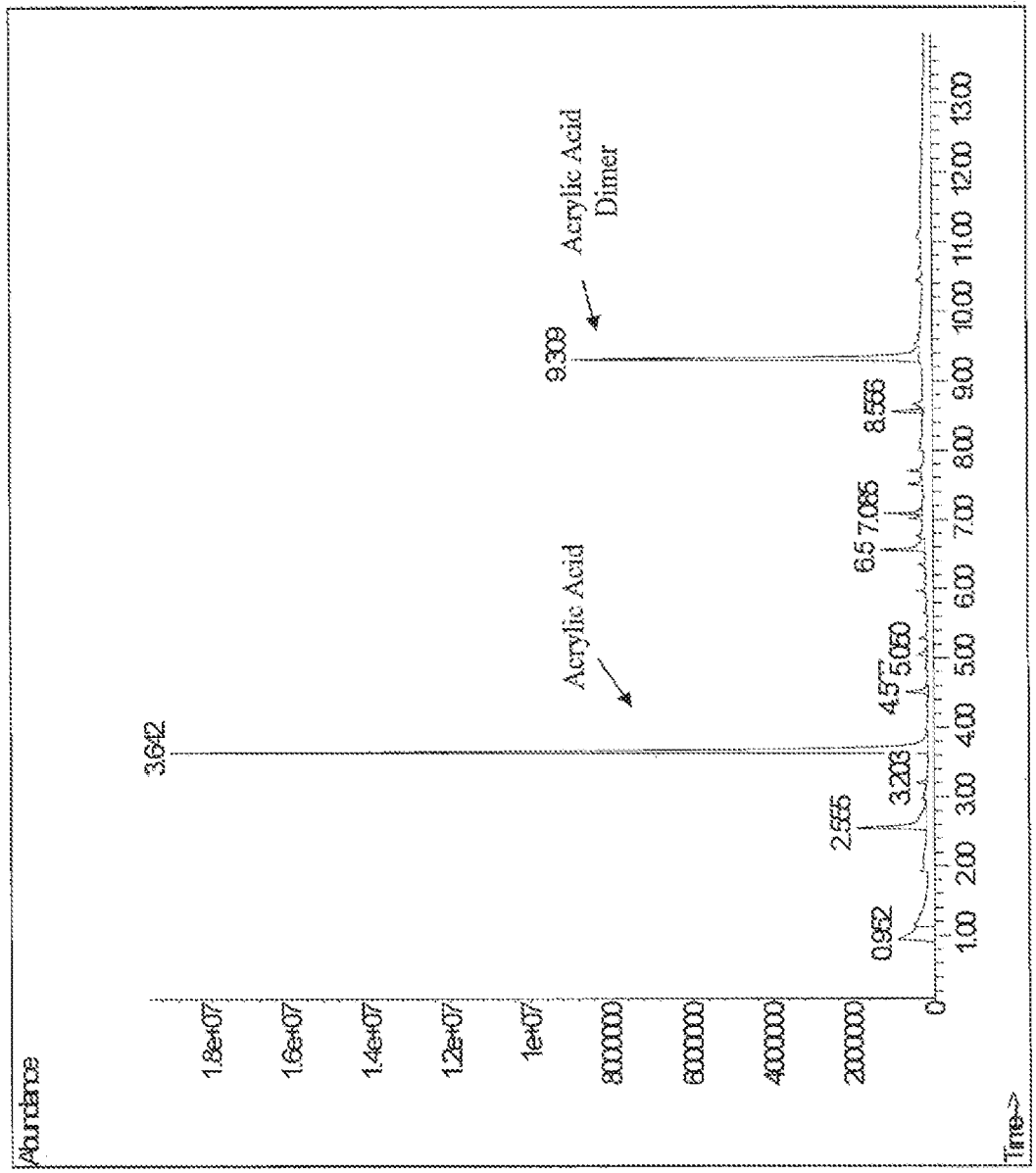
FIG. 11 is a gas chromatogram of dry switch grass+P3HP+$Na_2CO_3$ (5% by wt.) pyrolyzed at 300° C., according to one embodiment.

FIG. 9 shows the Py-GC-MS chromatogram for switch grass+poly-3HP with no catalyst present. The major peaks of interest generated from the poly-3HP were acrylic acid at 3.7 minutes and acrylic acid dimer at 9.3 minutes. FIGS. 10 and 11 show the Py-GC-MS chromatogram for switch grass+poly-3HP with the $Na_2CO_3$ and $FeSO_4$ catalysts respectively. The production of acrylic acid dimer during pyrolysis of poly-3HP was not unexpected as acrylic acid is very reactive at high temperatures even in the presence of polymerization inhibitors. However, it was found that generation of the acrylic acid dimer was minimized more effectively in the presence of the hydrated iron sulfate catalyst as compared to the sodium carbonate catalyst. Higher pyrolysis temperatures were also found to minimize acrylic acid dimer generation.

Example 8

Generation of Glycolide from the Pyrolysis of a Genetically Engineered Microbe Producing Poly-Glycolic Acid The addition of excess metal salts to fermentation broths containing the PHA biopolymer poly-glycolic acid (PGA) are expected to have the same effect during pyrolysis at 300° C. as demonstrated for poly-5HV in Example 6. PGA when subjected to pyrolysis from about 200° C. to about 350° C. will unzip the PGA at the ω-OH chain end of the polymer to form glycolide monomer or dimer components.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of producing a lower alkyl acrylate from a poly-3-hydroxybutyrate biomass obtained from genetically modified organisms, comprising:
   (A) producing biobased crotonic acid from the poly-3-hydroxybutyrate biomass by:
      (1) heating the poly-3-hydroxybutyrate biomass in the presence of a pyrolysis catalyst under suitable pyrolysis conditions to produce the crotonic acid from the poly-3-hydroxybutyrate biomass, wherein the heating is performed for no more than 5 minutes at a temperature from 230° C. to about 350° C. or at a temperature greater than 500° C. for no more than 20 seconds and wherein the crotonic acid yield is at least about 70% based on one gram of crotonic acid per gram of poly-3-hydroxybutyrate; and
      (2) recovering the crotonic acid, thereby producing the biobased crotonic acid
   and
   (B) producing the lower alkyl acrylate from the biobased crotonic acid by:
      (1) reacting the biobased crotonic acid with a lower alkyl alcohol under suitable conditions to form a lower alkyl crotonate ester, and isolating the lower alkyl crotonate ester;
      (2) reacting ethylene with 2-butene in the presence of a second metathesis catalyst under suitable conditions to produce propylene, and isolating propylene;
      (3) reacting the lower alkyl crotonate ester via cross-metathesis with a sufficient amount of propylene in the presence of a first metathesis catalyst under suitable conditions to form the lower alkyl acrylate and the 2-butene, and isolating the lower alkyl acrylate; and
      (4) recovering 2-butene, thereby producing recovered 2-butene, and feeding the recovered 2-butene as a starting material in reaction (B)(2),
   wherein the lower alkyl is a C2-C4 alkyl.

2. The method of claim 1, further comprising drying the poly-3-hydroxybutyrate biomass prior to heating to produce a dried poly-3-hydroxybutyrate biomass.

3. The method of claim 1, wherein the poly-3-hydroxybutyrate biomass is from a recombinant host selected from a plant crop, bacteria, a yeast, a fungus, an algae, a cyanobacteria, or a mixture of any two or more thereof.

4. The method of claim 3, wherein the host is bacteria.

5. The method of claim 4, wherein the bacteria is selected from *Escherichia coli, Alcaligenes eutrophus* (renamed as *Ralstonia eutropha*), *Bacillus* spp., *Alcaligenes latus, Azotobacter, Aeromonas, Comamonas, Pseudomonads, Pseudomonas, Ralstonia, Klebsiella*), *Synechococcus* sp PCC7002, *Synechococcus* sp. PCC 7942, *Synechocystis* sp. PCC 6803, *Thermosynechococcus elongatus* BP-I, *Chlorobium tepidum, Chloroflexusauranticus, Chromatium tepidum, Chromatium vinosum, Rhodospirillumrubrum, Rhodobacter capsulatus*, and *Rhodopseudomonas palustris*.

6. The method of claim 3, wherein the host is a plant crop.

7. The method of claim 6, wherein the plant crop is selected from tobacco, sugarcane, corn, switchgrass, miscanthus sorghum, sweet sorghum, or a mixture of any two or more thereof.

8. The method of claim 2, wherein the drying is at a temperature of 100° C. to 175° C.

9. The method of claim 2, wherein the dried poly-3-hydroxybutyrate biomass has a water content of 5 wt %, or less.

10. The method of claim 1, wherein the duration of heating is for about 1 minute to no more than 5 minutes.

11. The method of claim 1, wherein the duration of heating is from 1 minute to 2 minutes.

12. The method of claim 1, wherein the pyrolysis catalyst is a metal catalyst or an organic catalyst.

13. The method of claim 1, wherein the first metathesis catalyst is not exposed to ethylene.

14. The method of claim 1, wherein the first metathesis catalyst is a Hoveyda-Grubb's cross metathesis catalyst.

15. The method of claim 14, wherein the first metathesis catalyst is 1,3-bis(2,4,6-trimethylphenyl)-2-imidazolidinylidene)dichloro(o-isopropoxyphenylmethylene)ruthenium.

16. The method of claim 1, wherein the lower alkyl is butyl.

17. The method of claim 1, wherein the poly-3-hydroxybutyrate biomass comprises a co-polymer of 3-hydroxybutyrate.

18. The method of claim 1, wherein the heating is pyrolysis, torrefaction or flash pyrolysis.

19. The method of claim 1, wherein the biomass is from a recombinant algae selected from *Chlorella minutissima, Chlorella emersonii, Chlorella sorokiniana, Chlorella ellipsoidea, Chlorella* sp., or *Chlorella protothecoides*.

20. The method of claim 1, wherein the poly-3-hydroxybutrate biomass has an increased amount of poly-3-hydroxybutyrate production compared to that of wild-type organism.

21. The method of claim 1 wherein the heating is performed at a temperature of 230° C. to about 245° C. for no more than 5 minutes.

* * * * *